US009896496B2

(12) United States Patent
Madsen et al.

(10) Patent No.: US 9,896,496 B2
(45) Date of Patent: Feb. 20, 2018

(54) DERIVATIVE OF AN INSULIN ANALOGUE

(71) Applicant: Novo Nordisk A/S, Bagsvaerd (DK)

(72) Inventors: Peter Madsen, Bagsvaerd (DK); Tina Moeller Tagmose, Ballerup (DK); Helle Naver, Alleroed (DK); Thomas Boerglum Kjeldsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/023,872

(22) PCT Filed: Oct. 3, 2014

(86) PCT No.: PCT/EP2014/071236
§ 371 (c)(1),
(2) Date: Mar. 22, 2016

(87) PCT Pub. No.: WO2015/052088
PCT Pub. Date: Apr. 16, 2015

(65) Prior Publication Data
US 2016/0215037 A1  Jul. 28, 2016

(30) Foreign Application Priority Data
Oct. 7, 2013 (EP) .................................... 13187626

(51) Int. Cl.
C07K 14/62 (2006.01)
A61K 38/00 (2006.01)

(52) U.S. Cl.
CPC .............. *C07K 14/62* (2013.01); *A61K 38/00* (2013.01)

(58) Field of Classification Search
CPC ................................ C07K 14/62; A61K 38/28
See application file for complete search history.

(56) References Cited

U.S. PATENT DOCUMENTS

| | | | |
|---|---|---|---|
| 2,832,685 A | 4/1958 | Scott | |
| 3,528,960 A | 9/1970 | Haas | |
| 3,719,655 A | 3/1973 | Jackson et al. | |
| 3,869,437 A | 3/1975 | Lindsay et al. | |
| 3,950,517 A | 4/1976 | Lindsay et al. | |
| 4,033,941 A | 7/1977 | Stilz et al. | |
| 4,179,337 A | 12/1979 | Davis et al. | |
| 5,149,777 A | 9/1992 | Hansen et al. | |
| 5,179,189 A | 1/1993 | Domb et al. | |
| 5,359,030 A | 10/1994 | Ekwuribe | |
| 5,446,020 A | 8/1995 | Andy et al. | |
| 5,478,575 A | 12/1995 | Miyazaki et al. | |
| 5,506,202 A | 4/1996 | Vertesy et al. | |
| 5,506,203 A | 4/1996 | Backstrom et al. | |
| 5,597,796 A | 1/1997 | Brange | |
| 5,716,927 A | 2/1998 | Balschmidt et al. | |
| 5,898,067 A | 4/1999 | Balschmidt et al. | |
| 5,922,675 A | 7/1999 | Baker et al. | |
| 6,221,837 B1 | 4/2001 | Ertl et al. | |
| 6,251,856 B1 | 6/2001 | Markussen et al. | |
| 6,475,795 B1 | 11/2002 | Turley et al. | |
| 6,500,645 B1 | 12/2002 | Kjeldsen et al. | |
| 6,746,853 B1 | 6/2004 | Dahiyat et al. | |
| 6,770,625 B2 | 8/2004 | Soltero et al. | |
| 6,867,183 B2 | 3/2005 | Soltero et al. | |
| 6,869,930 B1 | 3/2005 | Havelund et al. | |
| 7,030,082 B2 | 4/2006 | Soltero et al. | |
| 7,030,083 B2 | 4/2006 | Schreiner et al. | |
| 9,018,161 B2 | 4/2015 | Nielsen et al. | |
| 2002/0045731 A1 | 4/2002 | Schaffer et al. | |
| 2002/0198140 A1 | 12/2002 | Havelund | |
| 2003/0027748 A1 | 2/2003 | Ekwuribe et al. | |
| 2003/0035775 A1 | 2/2003 | Klibanov | |
| 2003/0083232 A1 | 5/2003 | Soltero et al. | |
| 2003/0104981 A1 | 6/2003 | Mandic | |
| 2003/0134294 A1 | 7/2003 | Sandford et al. | |
| 2003/0166508 A1 | 9/2003 | Zhang | |
| 2004/0038867 A1 | 2/2004 | Still et al. | |
| 2004/0097410 A1 | 5/2004 | Zheng et al. | |
| 2004/0198949 A1 | 10/2004 | Ekwuribe et al. | |
| 2004/0254119 A1 | 12/2004 | West et al. | |
| 2005/0276843 A1 | 12/2005 | Quay et al. | |
| 2006/0019874 A1 | 1/2006 | Radhakrishnan et al. | |
| 2006/0183668 A1 | 8/2006 | Jonassen et al. | |
| 2007/0096431 A1 | 5/2007 | Mochizuki et al. | |
| 2008/0076705 A1 | 3/2008 | Kodra et al. | |
| 2008/0171695 A1 | 7/2008 | Garibay et al. | |
| 2011/0105720 A1 | 5/2011 | Madsen et al. | |

FOREIGN PATENT DOCUMENTS

| | | |
|---|---|---|
| CN | 1390854 A | 1/2003 |
| EP | 214826 A2 | 3/1987 |
| EP | 265213 A2 | 4/1988 |
| EP | 376156 A2 | 7/1990 |
| EP | 511600 A2 | 11/1992 |
| EP | 544466 A1 | 6/1993 |
| EP | 712861 A2 | 5/1996 |

(Continued)

OTHER PUBLICATIONS

Kudvu & Basu ("Ultra-long-acting insulins for a lifestyle-related pandemic" Lancet (2011), 377, pp. 880-881).*
Jonassen et al. ("Design of the Novel Protraction Mechanism of Insulin Degludec, an Ultra-long-Acting Basal Insulin" Pharm Res (2012) 29:2104-2114).*
Bennett, R.G., et al, "Insulin inhibition of the proteasome is dependent on degradation of insulin by insulin-degrading enzyme" Journal of Endocrinology, 2003, vol. 177, pp. 399-405.
Seabright, Paul J et al. Biochemical Journal, "The Characterization of Endosomal Insulin Degradation Intermediates and Their Sequence of Production", 1996, vol. 320, No. 3, pp. 947-956.
Schilling et al., 1991, "Degradation of Insulin by Trypsin and Alpha Chymotrypsin," Pharmaceutical Research 8 (6):721-727.
Brange et al. ("Design of Novel Insulins with Changed Self-Association and Ligand Binding Properties," GBF Monographs, 1989, 12, 139-144).

(Continued)

*Primary Examiner* — Christina Bradley
(74) *Attorney, Agent, or Firm* — Jianjie Hu

(57) ABSTRACT

The present invention provides a novel derivative of an analogue of human insulin, useful for the treatment of diabetes.

15 Claims, No Drawings

(56) References Cited

FOREIGN PATENT DOCUMENTS

| | | |
|---|---|---|
| EP | 712862 A2 | 5/1996 |
| EP | 837072 A2 | 4/1998 |
| EP | 925792 A2 | 6/1999 |
| EP | 1121144 A1 | 4/2000 |
| EP | 1002547 A1 | 5/2000 |
| EP | 0894095 | 5/2003 |
| GB | 1492997 A | 11/1977 |
| JP | 57-067548 A | 4/1982 |
| JP | H01254699 A | 10/1989 |
| JP | H03504240 A | 9/1991 |
| JP | H03-506023 A | 12/1991 |
| JP | H09502867 A | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2001-521004 A | 11/2001 |
| JP | 2001-521006 A | 11/2001 |
| JP | 2001-521904 A | 11/2001 |
| JP | 2002-308899 A | 10/2002 |
| JP | 2002-543092 A | 12/2002 |
| JP | 2003-518917 A | 6/2003 |
| RU | 2146139 C1 | 3/2000 |
| WO | 8910937 A1 | 11/1989 |
| WO | 90/01038 A1 | 2/1990 |
| WO | 90/12814 A1 | 11/1990 |
| WO | 91/12817 A1 | 9/1991 |
| WO | 92/00321 A1 | 1/1992 |
| WO | 92/000322 A1 | 1/1992 |
| WO | 92/01476 A1 | 2/1992 |
| WO | 92/012999 A1 | 8/1992 |
| WO | 94/08599 A1 | 4/1994 |
| WO | 95/07931 A1 | 3/1995 |
| WO | 95/13795 A1 | 5/1995 |
| WO | 95/24183 A1 | 9/1995 |
| WO | 96/15803 A1 | 5/1996 |
| WO | 96/29344 | 9/1996 |
| WO | 96/37215 A1 | 11/1996 |
| WO | 97/31022 A1 | 8/1997 |
| WO | 98/01473 A1 | 1/1998 |
| WO | 98/02460 A1 | 1/1998 |
| WO | 99/21888 A1 | 5/1999 |
| WO | 99/24071 A1 | 5/1999 |
| WO | 99/65941 A1 | 12/1999 |
| WO | 00/00176 A1 | 1/2000 |
| WO | 00/10541 A1 | 3/2000 |
| WO | 00/23098 A1 | 4/2000 |
| WO | 00/43034 A2 | 7/2000 |
| WO | 0042993 A2 | 7/2000 |
| WO | 00/61178 A1 | 10/2000 |
| WO | 00/69901 A2 | 11/2000 |
| WO | 00/78302 A1 | 12/2000 |
| WO | 02/094200 A2 | 11/2002 |
| WO | 02098232 | 12/2002 |
| WO | 02098446 A1 | 12/2002 |
| WO | 03/013573 | 2/2003 |
| WO | 03/022208 A2 | 3/2003 |
| WO | 03/022996 A2 | 3/2003 |
| WO | 03/047493 A2 | 6/2003 |
| WO | 03/048195 A2 | 6/2003 |
| WO | 03/053339 A2 | 7/2003 |
| WO | 03/094951 A1 | 11/2003 |
| WO | 03/094956 A1 | 11/2003 |
| WO | 04/105790 A1 | 12/2004 |
| WO | 05/005477 A2 | 1/2005 |
| WO | 05/012346 A1 | 2/2005 |
| WO | 05/012347 A2 | 2/2005 |
| WO | 05/016312 A1 | 2/2005 |
| WO | 2005/027978 A1 | 3/2005 |
| WO | 05/047508 A1 | 5/2005 |
| WO | 05/049061 A2 | 6/2005 |
| WO | 05/055976 A2 | 6/2005 |
| WO | 05/058961 A2 | 6/2005 |
| WO | 05/092301 A1 | 10/2005 |
| WO | 06/023943 A1 | 3/2006 |
| WO | 2006060753 A2 | 6/2006 |
| WO | 06/079641 A2 | 8/2006 |
| WO | 06/082204 A1 | 8/2006 |
| WO | 06/082205 A1 | 8/2006 |
| WO | 2006/079641 A2 | 8/2006 |
| WO | 06/097521 A1 | 9/2006 |
| WO | 07/006320 A1 | 1/2007 |
| WO | 07/041481 A1 | 4/2007 |
| WO | 07/047948 A2 | 4/2007 |
| WO | 07/074133 A2 | 7/2007 |
| WO | 2007/081824 A2 | 7/2007 |
| WO | 2007/096332 A1 | 8/2007 |
| WO | 2007/096431 A1 | 8/2007 |
| WO | 07/104737 A1 | 9/2007 |
| WO | 07/128815 A1 | 11/2007 |
| WO | 07/128817 A2 | 11/2007 |
| WO | 2008/015099 A2 | 2/2008 |
| WO | 2008/034881 A1 | 3/2008 |
| WO | 2008/132229 A2 | 11/2008 |
| WO | 2008/145730 A1 | 12/2008 |
| WO | 2008/152106 A1 | 12/2008 |
| WO | 2009/010428 A1 | 1/2009 |
| WO | 09/022005 A1 | 2/2009 |
| WO | 39/022006 A1 | 2/2009 |
| WO | 2009/112583 A2 | 9/2009 |
| WO | 2009/115469 A1 | 9/2009 |
| WO | 2010/049488 A1 | 5/2010 |
| WO | 2011161124 A1 | 12/2011 |
| WO | 2011161125 A1 | 12/2011 |

OTHER PUBLICATIONS

Ying-Chi Chu et al. "The A14 Position of Insulin Tolerates Cinsiderable Structural Alterations with Modest Effects on the Biological Behavior of the Hormone," Journal of Protein Chemistry, 1992, vol. 11, pp. 571-577.

Yip, C.C. et al. "Structure and function of Insulin: Preparation and Biological Activity of Guinea Pig DES-B-ASP30, DES-A-ASN21-Insulin." Canadian Journal of Biochemistry, 1976, vol. 54 pp. 866-871.

Stentz, F.B. et al., "Identification of Insulin Intermediates and Sites of Cleavage of Native Insulin by Insulin Protease from Human Fibroblasts," Journal of Biological Chemistry, 1989, vol. 264, No. 34 pp. 20275-20282.

Baker et al., Philosophical Transactions of the Royal Society of London, 1988, vol. 319, pp. 369-456.

Ward et al., Bioessays, 2009, vol. 31, pp. 422-434.

Seino et al., Biochemical and Biophysical Research Communications, 1989, vol. 159, pp. 312-316.

Moller et al., Molecular Endocrinology, 1989, vol. 3, No. 8, pp. 1263-1269.

Mosthaf et al., The EMBO Journal, 1990, vol. 9, pp. 2409-2413.

Yamaguchi et al., Endocrinology, 1991, vol. 129, No. 4, pp. 2058-2066.

Yamaguchi et al., Endocrinology, 1993, vol. 132, No. 3, pp. 1132-1138.

Blundell et al., Advances in Protein Chemistry, 1972, vol. 26, pp. 279-402.

Pullen et al., Nature, 1976, vol. 259, pp. 369-373.

Nakagawa et al., Journal of Biological Chemistry, 1987, vol. 262, No. 25, pp. 12054-12058.

Mirmira et al., The Journal of Biological Chemistry, 1991, vol. 266, No. 3, pp. 1428-1436.

Xu et al., Biochemistry, 2004, vol. 43, pp. 8356-8372.

De Meyts et al., Biochemical and Biophysical Research Communications, 1973, vol. 55, pp. 154-161.

Kurose et al., Journal of Biological Chemistry, 1994, vol. 269, No. 46, pp. 29190-29197.

Shoelson et al., Journal of Biological Chemistry, 1993, vol. 268, No. 6, pp. 4085-4091.

Zakova et al., Biochemistry, 2008, vol. 47, p. 5858-5868.

Fischer et al., Biological Chemistry, 1985, vol. 366, pp. 521-525.

Hua et al., Nature, 1991, vol. 354, pp. 238-241.

Ludvigsen et al., Jouronal of Molecular Biology, 1998, vol. 279, pp. 1-7.

(56) References Cited

OTHER PUBLICATIONS

Nakagawa et al., Biochemistry, 1992, vol. 31, pp. 3204-3214.
Markussen et al., International Journal of Peptide and Protein Research, 1985, vol. 26, No. 1, pp. 70-77.
Shoelson et al., Nature, 1983, vol. 302, pp. 540-543.
Glendorf et al., Biochemistry, 2008, vol. 47, pp. 4743-4751.
Soos et al., Biochemical Journal, 1986, vol. 235, No. 1, pp. 199-208.
Slaaby et al., Journal of Biological Chemistry, 2006, vol. 281, No. 36, pp. 25869-25874.
Volund, Biometrics, 1978, vol. 34, pp. 357-365.
Kabsch, Journal of Applied Crystallogrpahy, 1993, vol. 26, pp. 795-800.
Vagin et al., Journal of Applied Crystallography, 1997, vol. 30, pp. 1022-1025.
Murshudov, ACTA Crystallographica, 1997, vol. 53, pp. 240-255.
Emsley et al., ACTA Crystallographica, 2004, vol. 60, pp. 2126-2132.
Kjeldsen et al., Biotechnology and Genetic Engineering Reviews, 2001, vol. 18, pp. 89-121.
Schaffer, European Journal of Biochemistry, 1994, vol. 221, pp. 1127-1132.
Wells, Biochemistry, 1990, vol. 29, vol. 37, pp. 8509-8517.
Kaarsholm et al., Biochemistry, 1993, vol. 32, pp. 10773-10778.
Kristensen et al., Journal of Biological Chemistry, 2002, vol. 277, No. 21, pp. 18340-18345.
Mynarcik et al., Journal of Biological Chemistry, 1996, vol. 271, No. 5, pp. 2439-2442.
Whittaker, Journal of Biological Chemistry, 2005, vol. 280, No. 22, pp. 20932-20936.
Whittaker et al., Journal of Biological Chemistry, 2002, vol. 277, No. 49, pp. 47380-47384.
Frasca et al., Molecular and Cellular Biology, 1999, vol. 19, No. 5, pp. 3278-3288.
Kjeldsen et al., Proceedings of the National Academy of Sciences of the USA, 1991, vol. 88, No. 10, pp. 4404-4408.
Bajaj et al., "Coypu Insulin: Primary Structure, Conformation and Biological Properties of a Hystricomorph Rodent Insulin", Journal of Biochemistry, 1986, vol. 238, pp. 345-351.
Spoden M et al. International Journal of Peptide and Protein. "Structure-Function Relationships of DES-(B26-B30)-Insulin." 1995. vol. 46(3-4). pp. 221-227.
Chen, Y et al. Journal of Biological Chemistry. "In Vitro Refolding/Unfolding Pathways of Amphioxus Insulin-Like Peptide Implications for Folding Behavior of Insulin Family Proteins." 2004. vol. 279(53). pp. 55224-55233.
Smith, L.E., "Accession: P01337 1 [gi: 32172038] & Accession: P01337 2 [gi: 32172039], Definition: [Segment 1 of 2] Insulin-1 & [Segment 2 of 2] Insulin-1", NCBI Entrez Protein [online]; Mar. 21, 2006 uploaded, NCBI, [retrieved on Sep. 11, 2013], Retrieved from the internet:http://www.ncbi.nlm.nih.gov/protein/32172037?sat=34&satkey=10044352.
Aminlari et al., 1977, "Protein Dispersibility of Spray-Dried Whole Soybean Milk Base: Effect of Processing Variables," Journal of Food Science 42(4):985-988.
Bekerman et al., 2004, "Cyclosporin Nanoparticulate Liposphres for Oral Administration," Journal of Pharmaceutical Sciences 93(5):1264-1270.
Bennett et al., 2003, "Insulin Inhibition of the Proteasome is Dependent on Degradation of Insulin by Insulin-Degrading Enzyme," Journal of Endocrinology 177:399-405.
Bhatnagar et al., 2006, "Molecular Variants and Derivatives of Insulin for Improved Glycemic Control in Diabetes," Progress in Biophysics and Molecular Biology 91(3):199-228.
Chin et al., 1994, "Communication to the Editor: On Protein Solubility in Organic Solvents," Biotechnology and Bioengineering 44:140-145.
Foster et al., 1995, "Powder Characteristics of Proteins Spray-Dried From Different Spray-Driers," Drug Development and Industrial Pharmacy 21(15):1705-1723.

Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3)175-181.
Hashimoto et al., 1989, "Synthesis of Palmitoyl Derivatives of Insulin and Their Biological Activities" Pharmaceutical Research 6(2):171-176.
Havelund et al., 2004, "The Mechanism of Protraction of Insulin Detemir, a Long-Acting, Acylated Analog of Human Insulin" Pharmaceutical Research 21(8):1498-1504.
Hinds et al., 2000, "Synthesis and Characterization of Poly(Ethylene Glycol)-Insulin Conjugates," Bioconjugate Chemistry 11(2):195-201.
Hinds et al., 2002, "Effects of Peg Conjugation on Insulin Properties," Advanced Drug Delivery Reviews 54 (4):505-530.
Iwamoto, 2000, "New Insulin Formulation," Annual Review Endocrine Metabolism pp. 46-53.
Jonassen et al., 2006, "Synthesis of Palmitoyl Derivatives of Insulin and Their Biological Activities," Pharmaceutical Research 23(1):49-55.
Kochendoerfer et al., 2003, "Design and Chemical Synthesis of a Homogenous Polymer-Modified Erythropoiesis Protein," Science 299:884-887.
Kurtz et al., 1983, "Circulating IgG Antibody to Protamine in Patients Treated with Protamine-Insulins," Diabetologia 25(2):322-324.
Markussen et al., 1987, "Soluble, Prolonged-Acting Insulin Derivatives. I. Degree of Protraction, Crystallizability of Insulins Substituted in The . . . " Protein Engineering 1(3):205-213.
Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2(2):157-166.
Muranishi et al., 1992, "Trials of Lipid Modification of Peptide Hormones for Intestinal Delivery," Journal of Controlled Release 19:179-188.
Samuel et al., 1978, "Studies on the Immunogenicity of Protamines in Humans Andexperimental Animals by Means of a Micro-Complement Fixation Test," Clinical Experminemtal Immunology 33:252-260.
Schlichtkrull et al., 1956, "Insulin Crystals," Acta Chemica Scandinavica 10(9):1455-1458.
Toorisaka et al., 2004, "Emulsion-Based Drug Delivery Systems," Membrane 29(2):98-104 Abstract.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
L. Schaffer et al ,A novel high-affinity peptide antagonist to the insulin receptor.Journal: Biochemical and Biophysical Research Communications, Year 2008, vol. 376 , pp. 380-383.
L. Schäffer et al, Assembly of high-affinity insulin receptor agonists and antagonists from peptide building blocks, Journal :Proceedings of the National Academy of Sciences of the United States of America, Year 2003, vol. 100, pp. 4435-4439.
Riebel, U. et al,Equivalent in Vivo Biological Activity of Insulin Analogues and Human Insulin Despite Different in Vitro Potencies, Journal :Diabetes, Year 1990,vol. 39, pp. 1033-1039.
Hinds, K D et al. Advanced Drugs Delivery Reviews. "Effects of Peg Conjugation on Insulin Properties." 2002. vol. 54. pp. 505-530.
Chu Ying-Chi et al. Journal of Protein Chemistry. "The A14 Position of Insulin Tolesrates Considerable Structural Alterations With Modest Effects on the Biological Behavior of the Hormone." 1992. vol. 11(5). pp. 571-577.
Database Geneseq [Online] May 7, 1992 (May 7, 1992), "Modified human proinsulin with Gln A13 and Asp B17.", retrieved from EBI accession No. GSP:AAR20702 Database accession No. AAR20702.
Definition of hydrophobic and hydrophilic, Amino Acids, NJMS Department of Biochemistry and Molecular Biology. (http://njms2.umdnj.edu/biochweb/education/bioweb/PreK/AminoAcids.htm).

(56) References Cited

OTHER PUBLICATIONS

Hydrophobic Amino Acids, Molecular Cell Biology 6th edition (2008, W.H. Freeman and company) http://www.bio.miami.edu/tom/courses/protected/MCB6/ch02/2-14_part_1.jpg.
L. Schaffer et al, Assembly of high-affinity insulin receptor agonists and antagonists from peptide building blocks, Journal :Proceedings of the National Academy of Sciences of the United States of America, Year 2003, vol. 100, pp. 4435-4439.
The online Medical dictionary year 2005 Website:http://cancerweb.ncl.ac.uklomd/about.html, 5 pages, Jul. 7, 2005.
Joseph A. Affholter et al., "Identification of Residues in the Insulin Molecule Important for Binding to Insulin-Degrading Enzyme," Biochemistry, 1990, vol. 29, No. 33, pp. 7727-7733.

\* cited by examiner

DERIVATIVE OF AN INSULIN ANALOGUE

CROSS-REFERENCE TO RELATED APPLICATIONS

This application is a 35 U.S.C. § 371 National Stage application of International Application PCT/EP2014/071236 (published as WO 2015/052088), filed Oct. 3, 2014, which claimed priority of European Patent Application 13187626.0, filed Oct. 7, 2013, the contents thereof which are incorporated by reference in their entirety.

FIELD OF THE INVENTION

The present invention provides a novel derivative of an analogue of human insulin, useful for the treatment of diabetes.

SEQUENCE LISTING

The instant application contains a Sequence Listing which has been submitted in ASCII format via EFS-Web and is hereby incorporated by reference in its entirety. Said ASCII copy, created on Mar. 17, 2016, is named 8721US01_SeqList.txt and is 2 kilobytes in size.

BACKGROUND OF THE INVENTION

Insulin is a polypeptide hormone secreted by β-cells of the pancreas. Insulin consists of two polypeptide chains designated the A and B chains which are linked together by two inter-chain disulphide bridges. In human, porcine and bovine insulin, the A and B chains contains 21 and 30 amino acid residues, respectively. However, from species to species, there are variations among the amino acid residues present in the different positions in the two chains. The widespread use of genetic engineering has made it possible to prepare analogues of natural occurring insulins by exchanging, deleting and adding one or more of the amino acid residues. Insulin is used for the treatment of diabetes and diseases connected therewith or resulting from it.

For decades, insulin preparations with different duration of action have been developed and put on the market and general examples of such preparations are long-acting insulin preparations, medium acting insulin preparations and fast acting insulin preparations. Many patients take 2-4 injections per day, every week, every month, and every year, optionally for decades. No basal insulin products have to date been approved for administration less often than by daily subcutaneous injection. The discomfort of a large number of daily injections can, for example, be diminished by using insulin derivatives having an extremely long duration of action.

Various patent applications including WO 2010/049488 and WO 2011/161125 mention the possibility of administering insulin derivatives with long intervals. WO 2009/115469 relates to certain acylated protease stabilised insulins wherein at least one hydrophobic amino acid has been substituted with hydrophilic amino acids. It would be very desirable for diabetic patients, if basal insulin preparations for administration approximately once weekly were available.

OBJECTS OF THE INVENTION

The object of this invention is to overcome or ameliorate at least one of the disadvantages of the prior art, or to provide a useful alternative.

Another aspect of this invention relates to the furnishing of insulin derivatives with long pharmacokinetic (hereinafter PK) profiles, e.g. so that a subcutaneous treatment once a week or more seldom will be a satisfactory treatment of the diabetic patient's need for basal insulin treatment.

Another aspect of this invention relates to the furnishing of insulin derivatives with long PK profiles, e.g. PK profiles being longer than the PK profile of human insulin, after subcutaneous administration. In this connection, the PK profile can be determined as explained in Examples 5 and 6 herein.

Another aspect of this invention relates to the furnishing of insulin derivatives having a high solubility in an aqueous medium optionally containing zinc, e.g. a solubility which is higher than the solubility of human insulin. In this connection, the solubility can be determined as explained in Example 7 herein.

Another aspect of this invention relates to the furnishing of insulin derivatives which are soluble in an aqueous medium containing zinc, such as at least 5 zinc ions per insulin hexamer, when measured after storage at least 4 weeks at 37° C. or below after preparation. In this connection, the solubility may e.g. be determined as explained in Example 7 herein.

Another aspect of this invention relates to the furnishing of insulin derivatives which are soluble in an aqueous medium containing zinc, such as at least 5 zinc ions per insulin hexamer, when measured within 24-48 hours after preparation. In this connection, the solubility may be determined as explained in Example 7 herein.

Another aspect of this invention relates to the furnishing of insulin derivatives having good stability against enzymes, e.g. proteolytic enzymes, e.g. proteolytic enzymes present in the human stomach, e.g. pepsin, chymotrypsin and carboxypeptidase A. In this connection, the stability against enzymes can be determined as explained in Example 1 of WO 2008/034881.

Another aspect of this invention relates to the furnishing of insulin derivatives having good stability, especially chemical stability and physical stability, at storage, e.g. storage at 5° C. and at 30° C., for e.g. 2 years and for 2 weeks, respectively. In this connection, the chemical stability can be determined as explained in Examples 9 and 10 herein and the physical stability can be determined as explained in Examples 9 and 10 herein.

Another aspect of this invention relates to the furnishing of insulin derivatives which can efficiently be administered orally, e.g. once daily, to diabetic patients. Also, or alternatively, this invention relates to the furnishing of insulin derivatives which have a high oral bioavailability.

Another aspect of this invention relates to the furnishing of insulin derivatives having reduced daily fluctuations, e.g. variations between plasma concentrations ($C_{max}$ and $C_{min}$) following, e.g. once weekly subcutaneously administration.

Another aspect of this invention relates to the furnishing of insulin derivatives having reduced influence on the day-to-day variation in bioavailability following oral administration.

Another aspect of this invention relates to the furnishing of insulin derivatives having high potency, i.e. evoke a large response at low drug concentration, (drug activity expressed in terms of the amount required to produce an effect of given intensity).

Another aspect of this invention relates to the furnishing of insulin derivatives that bind very well to the insulin receptor. In this connection, the insulin receptor affinity can be determined as explained in Example 2 herein.

Another aspect of this invention relates to the furnishing of insulin derivatives having a low insulin receptor affinity. In this connection, the insulin receptor affinity can be determined as explained in Example 2 herein.

DEFINITIONS

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency. Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Herein, the naming of the insulins is done according to the following principles: The names are given as mutations and modifications (acylations) relative to human insulin. For the naming of the acyl moiety, the naming is done according to IUPAC nomenclature and in other cases as peptide nomenclature. For example, naming the acyl moiety:

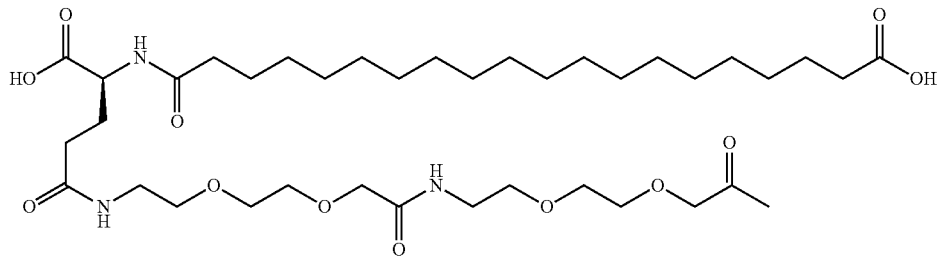 [SMILES: CC(=O)COCCOCCNC(=O)COCCOCCNC(=O)CC[C@H](NC(=O)CCCCCCCCCCCCCCCCCCC(=O)O)C(=O)O]

can for example be named "eicosanedioyl-γGlu-OEG-OEG", "eicosanedioyl-γGlu-2xOEG" or, "eicosanedioyl-gGlu-2xOEG" or "19-carboxynonadecanoyl-γGlu-OEG-OEG", wherein OEG is short hand notation for the amino acid $NH_2(CH_2)_2O(CH_2)_2OCH_2CO_2H$, [2-(2-aminoethoxy) ethoxy]acetic acid and γGlu (and gGlu) is short hand notation for the amino acid gamma glutamic acid in the L-configuration. Alternatively, the acyl moiety may be named according to IUPAC nomenclature (OpenEye, IUPAC style). According to this nomenclature, the above acyl moiety of the invention is assigned the following name: [2-[2-[2-[[2-[2-[2-[[(4S)-4-carboxy-4-(19-carboxynonadecanoylamino) butanoyl]amino]ethoxy]-ethoxy]acetyl]amino]ethoxy] ethoxy]acetyl].

For example, the insulin of Example 1 (with the sequence/structure given below) is named "A14E, B16E, B25H, B29K (N$^\epsilon$Eicosanedioyl-gGlu-2xOEG), desB30 human insulin" to indicate that the amino acid in position A14, Y in human insulin, has been mutated to E, the amino acid in position B16, Y in human insulin, has been mutated to E, the amino acid in position B25, F in human insulin, has been mutated to H, the amino acid in position B29, K as in human insulin, has been modified by acylation on the epsilon nitrogen in the lysine residue of B29, denoted N$^\epsilon$, by the residue eicosanedioyl-gGlu-2xOEG, and the amino acid in position B30, T in human insulin, has been deleted.

Asterisks in the formula below indicate that the residue in question is different (i.e. mutated) as compared to human insulin.

SEQ ID Nos: 1 and 2

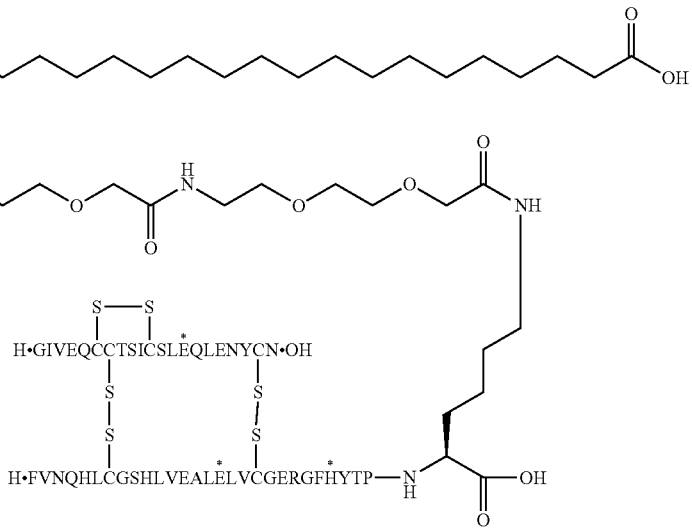

Alternatively, the insulins of the invention may be named according to IUPAC nomenclature (OpenEye, IUPAC style). According to this nomenclature, the insulin of Example 1 (i.e. Compound 1) is assigned the following name: N{Epsilon-B29}-[2-[2-[2-[[2-[2-[2-[[(4S)-4-carboxy-4-(19-carboxynonadecanoyl amino)butanoyl]amino]ethoxy]-ethoxy]acetyl]amino]ethoxy]ethoxy]acetyl]-[GluA14, GluB16, HisB25], des-ThrB30-Insulin(human).

SUMMARY OF THE INVENTION

This invention relates to a derivative of an insulin analogue, i.e. A14E, B16E, B25H, B29K(N(eps)eicosanedioyl-gGlu-2xOEG), desB30 human insulin (Compound 1).

DETAILED DESCRIPTION OF THIS INVENTION

It has, surprisingly, been found that A14E, B16E, B25H, B29K(N(eps)eicosanedioyl-gGlu-2xOEG), desB30 human insulin fulfils the above objects to a sufficient degree. For example, a subcutaneous treatment with Compound 1 once a week or more seldom will be a satisfactory treatment of the diabetic patient's need for basal insulin treatment. Furthermore, Compound 1 has a high solubility in an aqueous medium optionally containing zinc. In one aspect, Compound 1 has a solubility which is higher than the solubility of human insulin.

In one aspect, Compound 1 is soluble in an aqueous medium containing zinc such as at least 5 zinc ions per insulin hexamer, at least 6 zinc ions per insulin hexamer, at least 7 zinc ions per insulin hexamer, at least 8 zinc ions per insulin hexamer or at least 9 zinc ions per insulin hexamer, wherein the solubility is measured after storage at least 4 weeks at 37° C. or below after preparation.

In one aspect of the invention, Compound 1 is soluble in an aqueous medium containing zinc such as at least 5 zinc ions per insulin hexamer, at least 6 zinc ions per insulin hexamer, at least 7 zinc ions per insulin hexamer, at least 8 zinc ions per insulin hexamer, at least 9 zinc ions per insulin hexamer, at least 10 zinc ions per insulin hexamer, at least 11 zinc ions per insulin hexamer or at least 12 zinc ions per insulin hexamer, wherein the solubility is measured within 24-48 hours after preparation.

In one aspect, the solubility is determined as explained in Example 7 herein.

Pharmaceutical compositions containing Compound 1 can be prepared in a manner known per se, i.e., by using the excipients usually used in similar insulin compositions.

Injectable pharmaceutical compositions containing Compound 1 can be prepared using conventional techniques of the pharmaceutical industry which involve dissolving and mixing the ingredients as appropriate to give the desired end product. Thus, according to one procedure, Compound 1 is dissolved in an amount of water which is somewhat less than the final volume of the pharmaceutical composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

More precisely, an insulin preparation of this invention, for example a solution, may be prepared by dissolving Compound 1 in an aqueous medium at slightly acidic conditions. The aqueous medium is e.g. made isotonic by addition of a tonicity regulating agent. Furthermore, the aqueous medium may contain e.g. buffers, preservatives and zinc ions. The pH value of the solution is adjusted towards neutrality without getting too close to the isoelectric point of the compound of this invention in order to avoid potential precipitation. The pH value of the final insulin preparation depends upon the concentration of zinc ions, and the concentration of the compound of this invention. The insulin preparation is made sterile, for example, by sterile filtration.

A pharmaceutical composition may contain one or more excipients.

The term "excipient" broadly refers to any component other than the active therapeutic ingredient(s). The excipient may be an inert substance, an inactive substance, and/or a not medicinally active substance.

The excipient may serve various purposes depending on the pharmaceutical composition, e.g. as a carrier, vehicle, diluent, tablet aid, and/or to improve administration, and/or absorption of the active substance. Examples of excipients include, but is not limited to, diluents, buffers, preservatives, tonicity regulating agents (also known as tonicity agents or isotonic agents), chelating agents, surfactants, protease inhibitors, wetting agents, emulsifiers, antioxidants, bulking agents, metal ions, oily vehicles, proteins and/or a zwitterion and stabilisers.

The pharmaceutical composition of pharmaceutically active ingredients with various excipients is known in the art, see e.g. Remington: The Science and Practice of Pharmacy (e.g. $19^{th}$ edition (1995), and any later editions).

The insulin compositions are administered to the patients in a manner known per se, e.g. according to the general knowledge of the patient combined with the general knowledge of the physician. This invention is best used at the convenience of the patient. Therefore, specific administration intervals will be explored for each patient where dosages are administered less than daily. The final mode of use thus depends both on the product's capabilities and on the disposition and preference of the patient. This is due to the fact that the effect of any insulin product depends on the insulin need of the individual patient and the sensitivity to the pharmacodynamic actions of said insulin and lastly also to the preferences of the patient in a given situation. These conditions may change over time, both in terms of longer periods (years) and from day to day. The optimal dose level for any patient will depend on a variety of factors including the age, body weight, physical activity, and diet of the patient, on a possible combination with other drugs, and on the severity of the state to be treated. It is recommended that the dosage regimen be determined for each individual patient by those skilled in the art in a similar way as for known insulin compositions, however taking into consideration the present teachings concerning dosage intervals.

For the convenience of the patients, it is presumed that they prefer that the time interval (time lag) from the administration of Compound 1 to the next administration of Compound 1 has the same length, or approximately the same length, counted in number of days. It can even be expected that the patients will prefer that the administration of Compound 1 takes place once weekly, i.e., on the same day in the week, e.g. every Sunday. This will be an administration of Compound 1 every $7^{th}$ day and not more frequently on an average calculated for a period of time of 1 month, 6 months or 1 year. For some patients, it may be desirable to administer Compound 1 every $6^{th}$ day or approximately every $6^{th}$ day and not more frequently on an average calculated for a period of time of 1 month, 6 months or 1 year. For other patients, it may be desirable to administer Compound 1 every 5$^{th}$ day or approximately every 5$^{th}$ day and not more frequently on an average calculated for a period of time of 1 month, 6 months or 1 year. For other patients, it may be desirable to administer Compound 1 every 4$^{th}$ day or approximately every 4$^{th}$ day and not more frequently on an average calculated for a period of time of 1 month, 6 months or 1 year. Even other patients may find it advantageous to administer Compound 1 twice weekly, e.g. with an interval of about 3-4 days between each administration on an average calculated for a period of time of 1 month, 6 months or 1 year. For some patients, it may be desirable to administer Compound 1 every 3$^{rd}$ day or approximately every 3$^{th}$ day and not more frequently on an average calculated for a period of time of 1 month, 6 months or 1 year. For other patients, it may be desirable to administer Compound 1 every 2$^{nd}$ day or approximately every 2$^{nd}$ day and not more frequently on an average calculated for a period of time of 1 month, 6 months or 1 year. For some patients, it may be desirable to administer Compound 1 every 8$^{th}$ day or approximately every 8$^{th}$ day and not more frequently on an average calculated for a period of time of 1 month, 6 months or 1 year. Even other patients may not administer Compound 1 with a time interval of precisely the same length (counted in days), week after week, month after month or year after year. Some patients may administer Compound 1 sometime in the time interval from every 6$^{th}$ to every 8$^{th}$ day on an average calculated for a period of time of 1 month, 6 months or 1 year and not more frequently. Other patients may administer Compound 1 sometime in the time interval from every 5th to every 7$^{th}$ day on an average calculated for a period of time of 1 month, 6 months or 1 year and not more frequently. Even other patients may administer Compound 1 sometime in the time interval from every 4$^{th}$ to every 8$^{th}$ day on an average calculated for a period of time of 1 month, 6 months or 1 year and not more frequently. The time intervals mentioned here are to be understood as average time intervals within a period of time of say weeks, months or years. Here, it is intended that the term "day" covers 24 hours (i.e., a day and night) and, for the sake of easiness, a number of hours which is not divisible by 24 is to be rounded up to a whole number of days. Hence, e.g. 30 hours corresponds to 1 day and 40 hours corresponds to 2 days. The above mentioned administrations are parenterally.

The patients may have a daily basal insulin requirement of above about 0.2 IU/kg body weight/day and below about 1 IU/kg body weight/day and, furthermore, the patients may have a total (i.e., basal plus prandial) daily insulin requirement of above about 1 IU/kg body weight/day. However, these ranges may vary considerably from patient to patient and may for several patients be somewhat outside the ranges mentioned here.

Diseases and conditions which are the primary targets for this invention are diabetes mellitus (type 1 or 2) or other conditions characterized by hyperglycaemia, but also metabolic diseases and conditions in general where the metabolic effects of insulin has a clinical relevance or are of interest, such as pre-diabetes, impaired glucose tolerance, metabolic syndrome, obesity, cachexia, in vivo beta-cell loss/death, excessive appetite, and inflammation. All these types of conditions are known to or believed to benefit from a stable metabolic state in the subject who has the disease or condition. At any rate, any therapeutic regimen where administration of insulin is included may be modified by implementing the current teachings, meaning that such therapies will include administration of prolonged-profile-of-action insulins according to the teachings provided herein.

In order to exercise this invention, Compound 1 may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin composition orally, nasally or pulmonary, preferably in pharmaceutical compositions, powders or liquids, specifically designed for the purpose in question.

Alternatively, in order to exercise this invention, Compound 1 may be administered orally to patients in need of such a treatment. Oral administration may be performed by orally administering solid, semi-solid or liquid pharmaceutical compositions.

Embodiments of the method of this invention include those wherein administration of Compound 1 is supplemented with more frequent administrations of a fast-acting naturally occurring insulin, insulin analogue or insulin derivative and/or administration of a non-insulin anti-diabetic drug. In one embodiment of this invention, administration of Compound 1 is supplemented with administration of a non-insulin anti-diabetic drug, such as metformin.

PREFERRED FEATURES OF THIS INVENTION

To sum up and supplement the above statements, the features and clauses of this invention are as follows:

1. A14E, B16E, B25H, B29K(N(eps)eicosanedioyl-gGlu-2xOEG), desB30 human insulin (Compound 1).

2. A pharmaceutical composition comprising Compound 1.

3. Compound 1 for use as a medicament.

4. Compound 1 for use in the preparation of a pharmaceutical composition for the treatment or prevention of diabetes.

5. Compound 1 for use in the preparation of a pharmaceutical composition for the treatment or prevention of diabetes Type 1 and/or Type 2.

6. Compound 1 for use in the treatment of diabetes, wherein the compound is administered to the same patient every 2$^{nd}$ day or less frequently and, on average, during a period of time of at least 1 month, 6 months or 1 year, said compound is not administered more frequently to the same patient.

7. Compound 1 for use in the treatment of diabetes, wherein the compound is administered every 3$^{rd}$ day or less frequently, and, on average, during a period of time of at least 1 month, 6 months or 1 year, said compound is not administered more frequently to the same patient.

8. Compound 1 for use in the treatment of diabetes, wherein the compound is administered twice a week or less frequently, and, on average, during a period of time of at least 1 month, 6 months or 1 year, said compound is not administered more frequently to the same patient.

9. Compound 1 for use in the treatment of diabetes, wherein the compound is administered every 4$^{th}$ day or less frequently, and, on average, during a period of time of at least 1 month, 6 months or 1 year, said compound is not administered more frequently to the same patient.

10. Compound 1 for use in the treatment of diabetes, wherein the compound is administered every 5$^{th}$ day or less frequently, and, on average, during a period of time of at least 1 month, 6 months or 1 year, said compound is not administered more frequently to the same patient.

11. Compound 1 for use in the treatment of diabetes, wherein the compound is administered every 6$^{th}$ day or less frequently and, on average, during a period of time of at least 1 month, 6 months or 1 year, said compound is not administered more frequently to the same patient.

12. Compound 1 for use in the treatment of diabetes, wherein the compound is administered once weekly or less frequently and, on average, during a period of time of at least 1 month, 6 months or 1 year, said compound is not administered more frequently to the same patient.

13. Compound 1 for use in the treatment of diabetes, wherein the compound is administered every $8^{th}$ day or more frequently.

14. Compound 1 for use in the treatment of diabetes, wherein the compound is administered every $9^{th}$ day or more frequently.

15. Compound 1 for use in the treatment of diabetes, wherein the compound is administered every $10^{th}$ day or more frequently.

16. Compound 1 for use in the treatment of diabetes, wherein the compound is administered every $11^{th}$ day or more frequently.

17. Compound 1 for use in the treatment of diabetes, wherein the compound is administered every $12^{th}$ day or more frequently.

18. Compound 1 for use in the treatment of diabetes, wherein the compound is administered every $14^{th}$ day or more frequently.

19. Compound 1 for use in the treatment of diabetes, wherein the compound is administered every $21^{st}$ day or more frequently.

20. Compound 1 according to any one of clauses 6-19, wherein the currently or repeatedly treatment lasts for more than 1 month.

21. Compound 1 according to any one of clauses 6-19, wherein the currently or repeatedly treatment lasts for more than 2 month.

22. Compound 1 according to any one of clauses 6-19, wherein the currently or repeatedly treatment lasts for more than 3 month.

23. Compound 1 according to any one of clauses 6-19, wherein the currently or repeatedly treatment lasts for more than 1 year (one year).

24. Compound 1 according to any one of clauses 2-23, wherein the compound is administered parenteral, preferably subcutaneous, intramuscular or intravenous.

25. Compound 1 according to any one of clauses 2-23, wherein the compound is administered orally.

26. A method of treatment or prevention of diabetes, which method comprises administering to a subject in need thereof a therapeutically effective amount of Compound 1.

27. The method according to clause 26, which method comprises administering to a subject in need thereof a therapeutically effective amount of Compound 1 to the same patient every $2^{nd}$ day or less frequently and, on average, during a period of time of at least 1 month, 6 months or 1 year, said compound is not administered more frequently to the same patient.

28. The method according to clause 26, which method comprises administering to a subject in need thereof a therapeutically effective amount of Compound 1 to the same patient every $3^{rd}$ day or less frequently and, on average, during a period of time of at least 1 month, 6 months or 1 year, said compound is not administered more frequently to the same patient.

29. The method according to clause 26, which method comprises administering to a subject in need thereof a therapeutically effective amount of Compound 1 to the same patient twice a week or less frequently and, on average, during a period of time of at least 1 month, 6 months or 1 year, said compound is not administered more frequently to the same patient.

30. The method according to clause 26, which method comprises administering to a subject in need thereof a therapeutically effective amount of Compound 1 to the same patient every $4^{th}$ day or less frequently and, on average, during a period of time of at least 1 month, 6 months or 1 year, said compound is not administered more frequently to the same patient.

31. The method according to clause 26, which method comprises administering to a subject in need thereof a therapeutically effective amount of Compound 1 to the same patient every $5^{th}$ day or less frequently and, on average, during a period of time of at least 1 month, 6 months or 1 year, said compound is not administered more frequently to the same patient.

32. The method according to clause 26, which method comprises administering to a subject in need thereof a therapeutically effective amount of Compound 1 to the same patient every $6^{th}$ day or less frequently and, on average, during a period of time of at least 1 month, 6 months or 1 year, said compound is not administered more frequently to the same patient.

33. The method according to clause 26, which method comprises administering to a subject in need thereof a therapeutically effective amount of Compound 1 to the same patient once weekly or less frequently and, on average, during a period of time of at least 1 month, 6 months or 1 year, said compound is not administered more frequently to the same patient.

34. The method according to clause 26, which method comprises administering to a subject in need thereof a therapeutically effective amount of Compound 1 to the same patient every $8^{th}$ day or more frequently.

35. The method according to clause 26, which method comprises administering to a subject in need thereof a therapeutically effective amount of Compound 1 to the same patient $9^{th}$ every 9 day or more frequently.

36. The method according to clause 26, which method comprises administering to a subject in need thereof a therapeutically effective amount of Compound 1 to the same patient every $10^{th}$ day or more frequently.

37. The method according to clause 26, which method comprises administering to a subject in need thereof a therapeutically effective amount of Compound 1 to the same patient every $11^{th}$ day or more frequently.

38. The method according to clause 26, which method comprises administering to a subject in need thereof a therapeutically effective amount of Compound 1 to the same patient every $12^{th}$ day or more frequently.

39. The method according to clause 26, which method comprises administering to a subject in need thereof a therapeutically effective amount of Compound 1 to the same patient every $14^{th}$ day or more frequently.

40. The method according to clause 26, which method comprises administering to a subject in need thereof a therapeutically effective amount of Compound 1 to the same patient every $21^{st}$ day or more frequently.

41. The method according to clause 26, which method comprises administering to a subject in need thereof a therapeutically effective amount of Compound 1 to the same patient wherein the currently or repeatedly treatment for diabetes with Compound 1 lasts for more than 1 month.

42. The method according to clause 26, which method comprises administering to a subject in need thereof a therapeutically effective amount of Compound 1 to the same patient wherein the currently or repeatedly treatment for diabetes with Compound 1 lasts for more than 2 months.

43. The method according to clause 26, which method comprises administering to a subject in need thereof a therapeutically effective amount of Compound 1 to the same patient wherein the currently or repeatedly treatment for diabetes with Compound 1 lasts for more than 3 months.

44. The method according to clause 26, which method comprises administering to a subject in need thereof a therapeutically effective amount of Compound 1 to the same patient wherein the currently or repeatedly treatment for diabetes with Compound 1 lasts for more than 1 year (one year).

45. The method according to clause 26, which method comprises parenteral, preferably subcutaneous, intramuscular or intravenous, administering to a subject in need thereof a therapeutically effective amount of Compound 1 to the same patient.

46. The method according to clause 26, which method comprises orally administering to a subject in need thereof a therapeutically effective amount of Compound 1 to the same patient.

47. An aqueous solution comprising Compound 1.

48. An aqueous solution comprising Compound 1 and at least 5 zinc ions per insulin hexamer.

49. An aqueous solution comprising Compound 1 and at least 6 zinc ions per insulin hexamer.

50. An aqueous solution comprising Compound 1 and at least 7 zinc ions per insulin hexamer.

51. An aqueous solution comprising Compound 1 and at least 8 zinc ions per insulin hexamer.

52. An aqueous solution comprising Compound 1 and at least 9 zinc ions per insulin hexamer.

53. An aqueous solution comprising Compound 1 and at least 10 zinc ions per insulin hexamer.

54. An aqueous solution comprising Compound 1 and at least 11 zinc ions per insulin hexamer.

55. An aqueous solution comprising Compound 1 and at least 12 zinc ions per insulin hexamer.

56. The aqueous solution according to any one of clauses 47-55, wherein the pH is in the range of from 7 to 8.

57. The aqueous solution according to any one of clauses 47-55, wherein the pH is about 7.4.

58. A pharmaceutical composition comprising Compound 1, and one more excipients.

59. A pharmaceutical composition comprising Compound 1, and one more excipients selected from the group consisting of diluents, buffers, preservatives, tonicity regulating agents, chelating agents, surfactants, protease inhibitors, wetting agents, emulsifiers, antioxidants, bulking agents, metal ions, oily vehicles, proteins and/or a zwitterion and stabilisers.

60. The pharmaceutical composition according to clause 59, comprising at least 4.5 zinc ions per insulin hexamer.

61. The pharmaceutical composition according to clause 59, comprising at least 5 zinc ions per insulin hexamer.

62. The pharmaceutical composition according to clause 59, comprising at least 6 zinc ions per insulin hexamer.

63. The pharmaceutical composition according to clause 59, comprising at least 7 zinc ions per insulin hexamer.

64. The pharmaceutical composition according to clause 59, comprising at least 8 zinc ions per insulin hexamer.

65. The pharmaceutical composition according to clause 59, comprising at least 9 zinc ions per insulin hexamer.

66. The pharmaceutical composition according to clause 59, comprising at least 10 zinc ions per insulin hexamer.

67. The pharmaceutical composition according to clause 59, comprising at least 11 zinc ions per insulin hexamer.

68. The pharmaceutical composition according to clause 59, comprising at least 12 zinc ions per insulin hexamer.

69. The pharmaceutical composition according to any one of clauses 59-68, wherein the pH is in the range of from 7 to 8.

70. The pharmaceutical composition according to any one of clauses 59-68, wherein the pH is about 7.4.

71. The pharmaceutical composition according to any one of clauses 59-68, which is in the form of an aqueous solution.

72. The pharmaceutical composition according to any one of clauses 59-68, which is in the form of a tablet.

73. The pharmaceutical composition according to any one of clauses 59-68, which is in the form of a solid, semi-solid or liquid preparation, contained in a capsule such as a soft or a hard capsule.

74. Any novel product, apparatus, method or use defined by a feature and or a claim and/or a combination of features and/or claims described herein.

Any combination of two or more of the embodiments described herein is considered within the scope of the present invention.

EXAMPLES

The invention is further illustrated with reference to the following examples, which are not intended to be in any way limiting to the scope of the invention as claimed.

The following abbreviations are used herein:

| | |
|---|---|
| βAla is beta-alanyl; | MeCN is acetonitrile; |
| Aoc is 8-aminooctanoic acid; | OEG is [2-(2-aminoethoxy)ethoxy]ethylcarbonyl; |
| tBu is tert-butyl; | |
| DCM is dichloromethane; | Su is succinimidyl-1-yl = 2,5-dioxo-pyrrolidin-1-yl; |
| DIC is diisopropylcarbodiimide; | |
| DIPEA = DIEA is N,N-disopropylethylamine; | OSu is succinimidyl-1-yloxy = 2,5-dioxo-pyrrolidin-1-yloxy; |
| DMF is N,N-dmethylformamide; | RPC is reverse phase chromatography; |
| DMSO is dimethyl sulphoxide; | |
| EtOAc is ethyl acetate; | RT is room temperature; |
| Fmoc is 9-fluorenylmethyloxy-carbonyl; | TFA is trifluoroacetic acid; |
| | THF is tetrahydrofuran; |
| γGlu (gGlu) is gamma L-glutamyl; | TNBS is 2,4,6-trinitrobenzene-sulfonic acid; |
| DγGlu (DgGlu) is gamma D-glutamyl; | |
| HCl is hydrochloric acid; | TRIS is tris(hydroxymethyl)-aminomethane; and |
| HOAc is acetic acid; | TSTU is O-(N-succinimidyl)-1,1,3,3-tetramethyluronium tetrafluoroborate. |
| HOBt is 1-hydroxybenzotriazole; | |
| NMP is N-methylpyrrolidone; | |

The following examples and general procedures refer to intermediate compounds and final products identified in the specification and in the synthesis schemes. The preparation of the compound of the present invention is described in detail using the following examples, but the chemical reactions described are disclosed in terms of their general applicability to the preparation of compound of the invention. Occasionally, the reaction may not be applicable as described to each compound included within the disclosed scope of the invention. The compounds for which this occurs will be readily recognised by those skilled in the art. In these cases, the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Construction of vectors, yeast expression, processing and purification of insulin analogues can be done using the standard techniques readily recognised by those skilled in the art. One non-limiting example of preparation of insulin analogues was described previously (Glendorf T, Sørensen A R, Nishimura E, Pettersson I, & Kjeldsen T: Importance of the Solvent-Exposed Residues of the Insulin B Chain α-Helix for Receptor Binding; *Biochemistry* 2008 47 4743-4751). Briefly, mutations are introduced to insulin coding vectors using overlap extension PCR. Insulin analogues are expressed as proinsulin-like fusion proteins, with an Ala-Ala-Lys mini C-peptide in *Saccharomyces cerevisiae* strain MT663. The single-chain precursors are enzymatically converted into two-chain desB30 analogues using *A. lyticus* endoprotease. Full conversion to the two-chain desB30 analogue is verified by MALDI-TOF MS, and its purity is measured by RP-HPLC at both acidic and neutral pH.

The compound of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulin derivative in question etcetera, these modifications can readily be recognised and made by a person skilled in the art.

After acidic HPLC or desalting, the compounds are isolated by lyophilisation of the pure fractions. After neutral HPLC or anion exchange chromatography, the compounds are desalted, precipitated at isoelectrical pH, or purified by acidic HPLC.

Typical Purification Procedures

The HPLC system is a Gilson system consisting of the following: Model 215 Liquid handler, Model 322-H2 Pump and a Model 155 UV Dector. Detection is typically at 210 nm and 280 nm. The Âkta Purifier FPLC system (Amersham Biosciences) consists of the following: Model P-900 Pump, Model UV-900 UV detector, Model pH/C-900 pH and conductivity detector, Model Frac-950 Frction collector. UV detection is typically at 214 nm, 254 nm and 276 nm. Äkta Explorer Air FPLC system (Amersham BioGE Health Caresciences) consists of the following: Model P-900 Pump, Model UV-900 UV detector, Model pH/C-900 pH and conductivity detector, Model Frac-950 Fraction collector. UV detection is typically at 214 nm, 254 nm and 276 nm.

Acidic HPLC
Column: Phenomenex, Gemini, 5μ, C18, 110 Å, 250×30 cm
Flow: 20 mL/min
Eluent: A: 0.1% TFA in water,
 B: 0.1% TFA in CH$_3$CN
Gradient: 0-7.5 min: 10% B
 7.5-87.5 min: 10% B to 60% B
 87.5-92.5 min: 60% B
 92.5-97.5 min: 60% B to 100% B
Neutral HPLC
Column: Phenomenex, Gemini, C18, 5 μm 250×30.00 mm, 110 Å
Flow: 20 mL/min
Eluent: A: 20% CH$_3$CN in aqueous 10 mM TRIS+15 mM (NH$_4$)SO$_4$ pH=7.3
 B: 80% CH$_3$CN, 20% water Gradient: 0-7.5 min: 0% B
 7.5-52.5 min: 0% B to 60% B
 52.5-57.5 min: 60% B
 57.5-58 min: 60% B to 100% B
 58-60 min: 100% B
 60-63 min: 10% B
Anion exchange chromatography
Column: 150 mL (2.6×28 cm) Poros 50HQ
Flow: 25 mL/min
Eluent: A buffer: 15 mM TRIS, 50 mM Ammoniumacetat in 50% Ethanol, pH 7.5 (1.6 mS/cm)
 B buffer: 15 mM TRIS, 500 mM Ammoniumacetat in 50% Ethanol, pH 7.5 (14 mS/cm)
Gradient: 0-80% B over 20CV
Solid Phase Synthesis 19-((S)-1-carboxy-3-{2-[2-({2-[2-(2,5-dioxopyrrolidin-1-yloxycarbonylmethoxy)ethoxy]ethyl-carbamoyl}methoxy)ethoxy]ethylcarbamoyl}propylcarbamoyl)nonadecanoic acid Alternative Name: Eicosanedioyl-gGlu-OEG-OEG-OSu 19-((S)-1-carboxy-3-{2-[2-({2-[2-(2,5-dioxopyrrolidin-1-yloxycarbonylmethoxy)-ethoxy]ethylcarbamoyl}methoxy)ethoxy]ethylcarbamoyl}propylcarbamoyl)nonadecanoic acid can be synthesised on solid support using procedures well known to skilled persons in the art of solid phase peptide synthesis. This procedure e.g. comprises attachment of a Fmoc protected amino acid to a polystyrene 2-chlorotritylchloride resin. The attachment can, e.g. be accomplished using the free N-protected amino acid in the presence of a tertiary amine, like triethyl amine or N,N-diisopropylethylamine (see references below). The C-terminal end (which is attached to the resin) of this amino acid is at the end of the synthetic sequence being coupled to the parent insulins of the invention. After attachment of the Fmoc amino acid to the resin, the Fmoc group is deprotected using, e.g. secondary amines, like piperidine or diethyl amine, followed by coupling of another (or the same) Fmoc protected amino acid and deprotection. The synthetic sequence is terminated by coupling of a mono-tert-butyl protected fatty (α, ω) diacid, namely eicosanedioic acid mono-tert-butyl ester. Cleavage of the compounds from the resin is accomplished using diluted acid like 0.5-5% TFA/DCM (trifluoroacetic acid in dichloromethane), acetic acid (e.g. 10% in DCM, or HOAc/trifluoroethanol/DCM 1:1:8), or hecafluoroisopropanol in DCM (see e.g. "*Organic Synthesis on Solid Phase*", F. Z. Dörwald, Wiley-VCH, 2000. ISBN 3-527-29950-5; "*Peptides: Chemistry and Biology*", N. Sewald & H.-D. Jakubke, Wiley-VCH, 2002, ISBN 3-527-30405-3; and "*The Combinatorial Cheemistry Catalog*" 1999, Novabiochem AG; and references cited therein). This ensures that the tert-butyl ester present in the compound as carboxylic acid protecting groups is not deprotected. Finally, the C-terminal carboxy group (liberated from the resin) is activated, e.g. as the N-hydroxysuccinimide ester (OSu) and used either directly or after purification as coupling reagent, or after deprotection in attachment to A14E, B16E, B25H, desB30 human insulin.

Alternatively, the acylation reagents 19-((S)-1-carboxy-3-{2-[2-({2-[2-(2,5-dioxo-pyrrolidin-1-yloxycarbonyl-methoxy)ethoxy]ethylcarbamoyl}methoxy)ethoxy]ethyl-carbamoyl}-propylcarbamoyl)nonadecanoic acid can be prepared by solution phase synthesis:

The mono-tert-butyl protected fatty diacid, eicosanedioic acid mono-tert-butyl ester, is activated, e.g. as OSu-ester as described below or as any other activated ester known to those skilled in the art, such as HOBt- or HOAt-ester. This active ester is coupled with glutamic acid a-tert-butyl ester in a suitable solvent such as THF, DMF, NMP (or a solvent mixture) in the presence of a suitable base, such as DIPEA or triethylamine. The intermediate is isolated, e.g. by extractive procedures or by chromatographic procedures. The resulting intermediate is again subjected to activation (as described above) and to coupling with OEG-OEG ([2-(2-{2-[2-(2-Amino-ethoxy)-ethoxy]-acetylamino}-ethoxy)-ethoxy]-acetic acid) as described above followed by activation with TSTU to afford the acylation reagent 19-((S)-1-carboxy-3-{2-[2-({2-[2-(2,5-dioxopyrrolidin-1-yloxycarbonyl-methoxy)ethoxy]ethylcarbamoyl}methoxy)ethoxy]ethylcarbamoyl}propylcarbamoyl)-nonadecanoic acid.

The acylation reagent prepared by the above described methods may be tert-butyl de-protected after activation as OSu ester. This may be done by TFA treatment of the OSu-activated tert-butyl protected acylation reagent. After acylation of A14E,B16E,B25H,desB30 human insulin, the resulting unprotected acylated A14E,B16E,B25H,desB30 human insulin is obtained, e.g. as described in Example 1.

If the reagent prepared by any of the above methods is not tert-butyl de-protected after activation as OSu ester, acylation of A14E,B16E,B25H,desB30 human insulin affords the corresponding tert-butyl protected acylated A14E,B16E,B25H,desB30 human insulin. In order to obtain unprotected acylated A14E,B16E,B25H,desB30 human insulin, the protected insulin is to be de-protected. This can be done by TFA treatment to afford unprotected acylated A14E,B16E,B25H,desB30 human insulin.

Alternatively, the acylation reagent can be synthesised in solution using benzyl protection of the carboxylic acid groups as illustrated below.

19-((S)-1-Carboxy-3-{2-[2-({2-[2-(2,5-dioxo-pyrrolidin-1-yloxycarbonylmethoxy)ethoxy]-ethylcarbamoyl}methoxy)ethoxy]ethylcarbamoyl}propylcarbamoyl)nonadecanoic acid Alternative Name: Eicosanedioyl-gGlu-OEG-OEG-OSu LCMS Method (LCMS)

A Waters Micromass ZQ mass spectrometer was used to identify the mass of the sample after elution from a Waters Alliance HT HPLC system.
Eluents: A: 0.1% Trifluoroacetic acid in water
    B: 0.1% Trifluoroacetic acid in acetonitrile
Column: Phenomenex, Jupiter C4 50×4.60 mm, id: 5 μm
Gradient: 10%-90% B over 7.5 min at 1.0 mL/min
Column: Phenomenex, Jupiter 5μ C4 300 Å 50×4.60 mm
LC method: 10-90% B 10 min: A: 0.1% CH$_3$CN B: CH$_3$CN:
  0-7.5 min: 10-90% B
  7.5-8.5 min: 90-10% B
  8.5-9.5 min 10% B
  Flow: 1 mL/min
  9.5-10.00 min 10% B
  Flow: 0.1 mL/min Eicosanedioic Acid Tert-butyl Ester
N-hydroxysuccinimide Ester

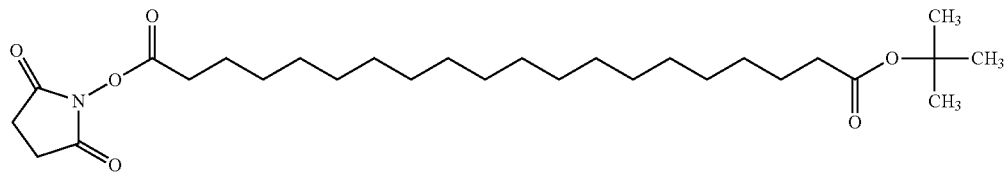 [SMILES: CC(C)(C)OC(=O)CCCCCCCCCCCCCCCCCCC(=O)ON1C(=O)CCC1=O]

Eicosanedioic acid mono-tert-butyl ester (5 g, 12.54 mmol) and TSTU (4.53 g, 15.05 mmol) were mixed in THF (50 mL), DIPEA (2.62 mL) was added and the resulting cloudy mixture was stirred at RT for 2 h, then DMF (30 mL) was added resulting in a clear solution which was further stirred overnight. The resulting mixture was evaporated to almost dryness and the residue was mixed with cold acetonitrile resulting in the precipitation of a precipitate. This was filtered off and dried in vacuo overnight, affording 6.01 g (97%) of eicosanedioic acid tert-butyl ester N-hydroxysuccinimide ester.

MS (electrospray): m/z: 440 (M−56 (tBu)).

(S)-2-(19-tert-Butoxycarbonylnonadecanoylamino)pentanedioic acid 1-tert-butyl ester

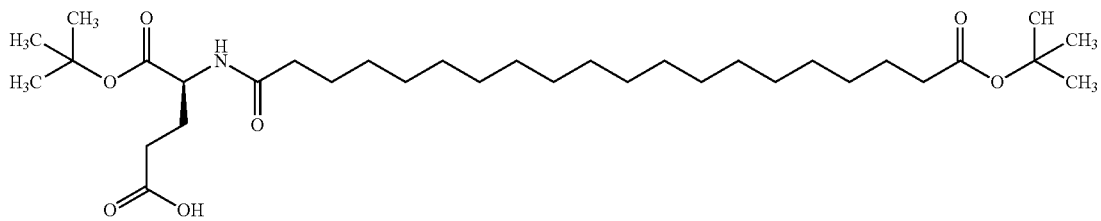 [SMILES: CC(C)(C)OC(=O)CCCCCCCCCCCCCCCCCCC(=O)N[C@@H](CCC(=O)O)C(=O)OC(C)(C)C]

Eicosanedioic acid tert-butyl ester 2,5-dioxo-pyrrolidin-1-yl ester (6.01 g, 12.124 mmol) was dissolved in THF (150 mL) and mixed with a slurry of H-Glu-OtBu (2.71 g, 13.33 mmol) in DMF/water (1/1, 40 mL). This resulted in a gel-like solution which was heated to give a clear solution that was stirred at RT for 3 hours. Then the solution was evaporated, 100 mL of water was added and the mixture was heated to 60° C. which resulted in a solution which crystallised on cooling. The precipitate was re-crystallised from acetonitrile and the crystals were dried in vacuum. Yield 6.82 g (96%).

MS (electrospray): m/z 584 (M+1).

(S)-2-(19-tert-Butoxycarbonylnonadecanoylamino)pentanedioic acid 1-tert-butyl ester 5-(2,5-dioxopyrrolidin-1-yl) ester

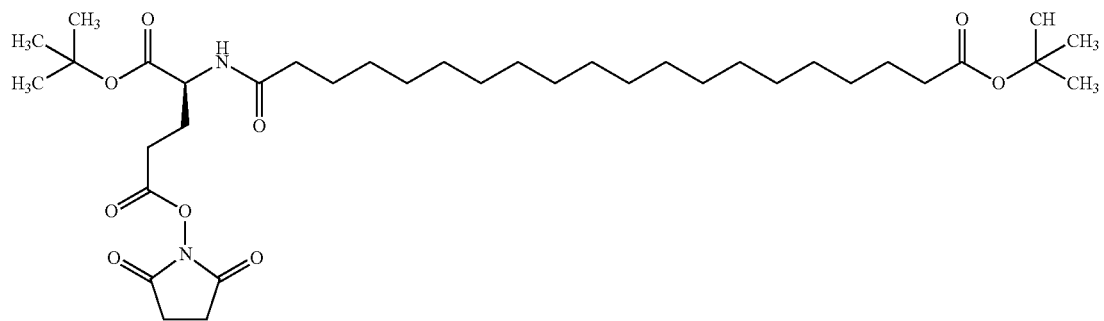 [SMILES: CC(C)(C)OC(=O)CCCCCCCCCCCCCCCCCCC(=O)N[C@@H](CCC(=O)ON1C(=O)CCC1=O)C(=O)OC(C)(C)C]

(S)-2-(19-tert-Butoxycarbonylnonadecanoylamino)pentanedioic acid 1-tert-butyl ester (6.52 g, 11.17 mmol) was dissolved in THF (100 mL), DIPEA (2.14 mL) was added followed by a solution of TSTU (3.70 g, 12.29 mmol) in acetonitrile (25 mL). The mixture was stirred overnight at RT, then it was evaporated, resulting in a brownish residue which was re-crystallised from acetonitrile. After cooling overnight at 5° C. a powder was formed. This was dissolved in THF and dried with MgSO$_4$, filtered and evaporated to dryness to afford 6.17 g (81%) of the title compound.

MS (electrospray): m/z: 681 (M+1).

19-{(S)-1-tert-Butoxycarbonyl-3-[2-(2-{[2-(2-carboxymethoxyethoxy)ethylcarbamoyl]-methoxy}ethoxy)ethylcarbamoyl]propylcarbamoyl}nonadecanoic acid tert-butyl ester (Alternative name: $^t$Bu-Eicosanedioyl-gGlu(O$^t$Bu)-OEG-OEG-OH)

To a solution of 2-(19-tert-Butoxycarbonylnonadecanoylamino)pentanedioic acid 1-tert-butyl ester 5-(2,5-dioxopyrrolidin-1-yl) ester (2.50 g) and [2-(2-{2-[2-(2-aminoethoxy)-ethoxy]acetylamino}ethoxy)ethoxy]acetic acid (alternative name: H-OEG-OEG-OH)(1.47 g) in ethanol (40 mL) was added DIPEA (1.26 mL). The mixture was stirred at room temperature overnight and then concentrated in vacuo. To the residue was added aqueous 0.1 N HCl (150 mL) and ethyl acetate (200 mL). The layers were separated and the aqueous layer was extracted with ethyl acetate (100 mL). The combined organic layers were washed with water and brine, dried (magnesium sulphate) and concentrated in vacuo to give an oil, which crystallised on standing.

Yield 96% (3.1 g). LCMS: Theoretical mass: 874.2. Found: 874.49.

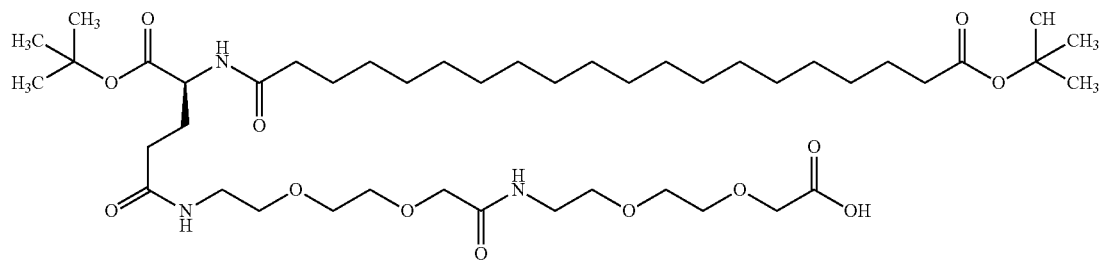 [SMILES: CC(C)(C)OC(=O)CCCCCCCCCCCCCCCCCCC(=O)N[C@@H](CCC(=O)NCCOCCOCC(=O)NCCOCCOCC(=O)O)C(=O)OC(C)(C)C]

19-((S)-1-tert-Butoxycarbonyl-3-{2-[2-({2-[2-(2,5-dioxo-pyrrolidin-1-yloxycarbonyl methoxy)-ethoxy]ethylcarbamoyl}methoxy)ethoxy]ethylcarbamoyl}propylcarbamoyl)nonadecanoic acid tert-butyl ester (Alternative name: ᵗBu-Eicosanedioyl-gGlu(OᵗBu)-OEG-OEG-OSu)

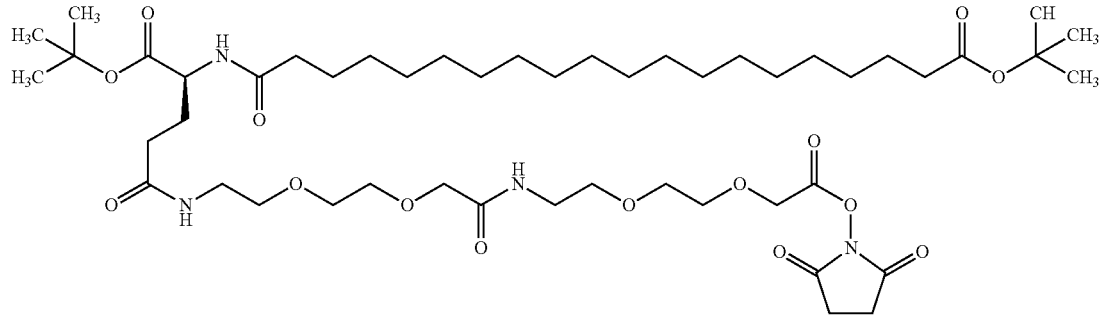 [SMILES: CC(C)(C)OC(=O)CCCCCCCCCCCCCCCCCCC(=O)N[C@@H](CCC(=O)NCCOCCOCC(=O)NCCOCCOCC(=O)ON1C(=O)CCC1=O)C(=O)OC(C)(C)C]

To a solution of 19-{(S)-1-tert-Butoxycarbonyl-3-[2-(2-{[2-(2-carboxymethoxy-ethoxy)ethylcarbamoyl]methoxy}ethoxy)ethylcarbamoyl]propylcarbamoyl}nonadecanoic acid tert-butyl ester (3.1 g) in acetonitrile (50 mL) was added TSTU (1.39 g) and DIPEA (0.91 mL). The mixture was stirred at room temperature overnight and then concentrated in vacuo. To the residue was added aqueous 0.1 N HCl (100 mL) and ethyl acetate (200 mL). The layers were separated and the aqueous layer was extracted with ethyl acetate (50 mL). The combined organic layers were washed with water and brine, dried (magnesium sulphate) and concentrated in vacuo to give an oil.

Yield 99% (3.4 g). LCMS: Theoretical mass: 971.2 Found: 971.8.

19-((S)-1-Carboxy-3-{2-[2-({2-[2-(2, 5-dioxo-pyrrolidin-1-yloxycarbonylmethoxy)ethoxy]ethylcarbamoyl}methoxy)ethoxy]ethylcarbamoyl}propylcarbamoyl)nonadecanoic acid Alternative Name: Eicosanedioyl-gGlu-OEG-OEG-OSu 19-((S)-1-tert-Butoxycarbonyl-3-{2-[2-({2-[2-(2, 5-dioxo-pyrrolidin-1-yloxycarbonylmethoxy)-ethoxy]ethylcarbamoyl}-methoxy)ethoxy]ethylcarbamoyl}propylcarbamoyl)nonadecanoic acid tert-butyl ester (3.4 g) was stirred in TFA (75 mL) for 45 min and then concentrated in vacuo. The residue was co-concentrated with toluene 3 times to give a solid. The residue was crystallised in 2-propanol and filtered to give a white crystalline compound.

Yield 80% (2.4 g). LCMS: Theoretical mass: 859.03 Found: 859.44.

For acylation of the lysine residue in position B29 (in the epsilon position) of A14E, B16E, B25H, desB30 human insulin, acylation is preferably performed at alkaline pH (e.g. at pH 10, 10.5, or 11). This is illustrated in Example 1 herein.

Example 1

N{Epsilon-B29}-[2-[2-[2-[[2-[2-[2-[[(4S)-4-carboxy-4-(19-carboxynonadecanoyl amino)butanoyl]amino]ethoxy]ethoxy]acetyl]amino]ethoxy]ethoxy]acetyl]-[GluA14,GluB16,HisB25],des-ThrB30-Insulin(human)

(Alternative name: A14E, B16E, B25H, B29K(Nᵉeicosanedioyl-gGlu-2xOEG), desB30 human insulin; Compound 1)

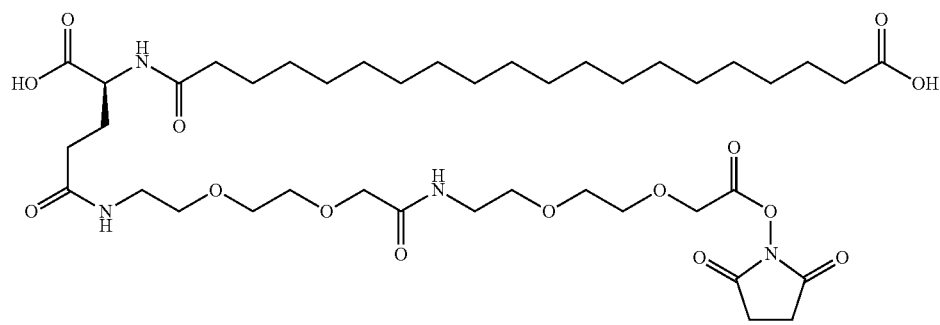 [SMILES: O=C(O)CCCCCCCCCCCCCCCCCCC(=O)N[C@@H](CCC(=O)NCCOCCOCC(=O)NCCOCCOCC(=O)ON1C(=O)CCC1=O)C(=O)O]

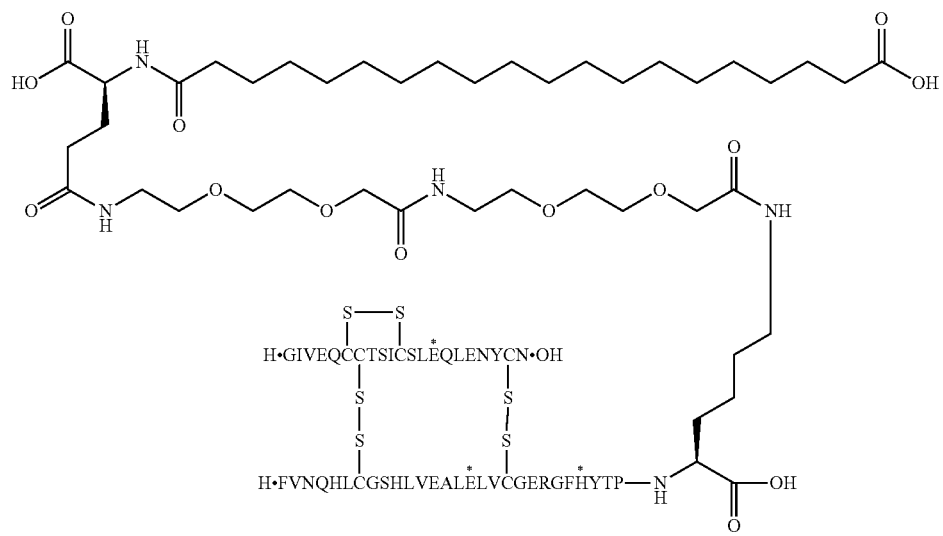

A14E, B16E, B25H, desB30 human insulin (3.0 g, 0.53 mmol) was dissolved in 150 mM aqueous Na$_2$CO$_3$ (40 mL) and 5 mL THF was added. The pH value was adjusted to 11.0 with 1M aqueous NaOH. Under vigorous stirring, 19-((S)-1-carboxy-3-{2-[2-({2-[2-(2,5-dioxopyrrolidin-1-yloxycarbonylmethoxy)ethoxy]ethylcarbamoyl}methoxy)ethoxy]-ethylcarbamoyl}propylcarbamoyl)nonadecanoic acid (641 mg, 0.75 mmol, prepared as described above) dissolved in a mixture of 1.5 mL THF and 1.5 mL DMF during one minute. While adding, pH was kept constant at 10.5-11 with addition of 1N aqueous NaOH. The mixture was stirred for one hour.

The pH value was adjusted to 7.5 with 1M HCl and 50% ethanol was added to a volume of 500 mL. The pH value was adjusted to 7.5. The conductivity was measured to 1.6 mS/Cm.

Purification was performed by anion exchange chromatography on an Äkta Explorer:
Column: 150 mL (2.6×28 cm) Poros 50HQ
A buffer: 15 mM TRIS, 50 mM ammonium acetate in 50% ethanol, pH 7.5 (1.6 mS/cm)
B buffer: 15 mM TRIS, 500 mM ammonium acetate in 50% ethanol, pH 7.5 (14 mS/cm)
Gradient: 0-80% B over 20CV
Flow: 25 mL/min.

The product pool, 700 mL, was diluted with 700 mL of 50% ethanol and purified once more:
Column: 150 mL (2.6×28 cm) Poros 50HQ
A buffer: 15 mM TRIS, 50 mM ammonium acetate in 50% ethanol, pH 7.5 (1.6 mS/cm)
B buffer: 15 mM TRIS, 500 mM ammonium acetate in 50% ethanol, pH 7.5 (14 mS/cm)
Gradient: 0-100% B over 12CV
Flow: 25 mL/min.

The product pool, 300 mL, was diluted with 300 mL water and desalted on a C18 column:
Column: 30×250 mm (Daiso_200_15 um_FEFgel304_ODDMS_30×250 mm), CV=177 mL
A Buffer: 10% acetonitrile in milli-Q water+0.1% TFA
B Buffer: 80% acetonitrile in milli-Q water+0.1% TFA
Gradient: 25-80% B over 20 min.
Flow: 35 mL/min.

The product fraction was freeze dried to afford the TFA salt, which was dissolved in 50 mL water plus 10 mL acetonitrile and pH was adjusted to 8.0 with 0.5M aqueous NaOH and freeze dried to afford 1.25 g (36%) of the title insulin.

LC-MS (electrospray): m/z=1593.1 (M+4)/4. Calculated: 1594.1.

Example 2

Insulin Receptor Affinity

The affinity of the acylated insulin analogues of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 mL of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 mL of SPA-beads and binding buffer to a total of 12 mL. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the Graph Pad Prism 2.01 (GraphPad Software, San Diego, Calif.) and affinities are expressed relative (in percentage (%)) to the affinity of human insulin.

A related assay is also used wherein the binding buffer also contains 1.5% HSA in order to mimic physiological conditions.

TABLE 1

Insulin receptor affinities of selected insulins of the invention

| Test compound | Relative IR-A affinity (0% HSA) (%) | Relative IR-A affinity (1.5% HSA) (%) |
|---|---|---|
| Compound 1 | 0.1 | 0.01 |

Example 3

Hydrophobicity of the Insulin Derivatives of the Invention

The hydrophobicity of an insulin derivative is found by reverse phase HPLC run under isocratic conditions. The elution time of the insulin derivative is compared to that of human insulin (herein designated HI) or another derivative with a known hydrophobicity under the same conditions. The hydrophobicity, k'rel, is calculated as: $k'rel_{deriv}=((t_{deriv}-t_0)/(t_{ref}-t_0))*k'rel_{ref}$. Using HI as reference: $k'rel_{ref}=k'rel_{HI}=1$. The void time of the HPLC system, $t_0$, is determined by injecting 5 µl of 0.1 mM NaNO$_3$.

Running conditions:
Column: Lichrosorb RP-C18, 5 µm, 4×250 mm
Buffer A: 0.1 M natrium phosphate pH 7.3, 10 vol % CH$_3$CN
Buffer B: 50 vol % CH$_3$CN
Injection volume: 5 µl
Run time: Maximum 60 minutes After running an initial gradient, the isocratic level for running the derivative and reference (for example HI) is chosen, and the elution times of the derivative and reference under isocratic conditions are used in the above equation to calculate $k'rel_{deriv}$.

TABLE 2

Hydrophobicity of the insulin derivatives of the invention

| Test compound | Relative hydrophobicity $k'rel_{deriv}$ |
|---|---|
| Compound 1 | 0.6 |

Example 4

Degradation of Insulin Analogues Using Duodenum Lumen Enzymes

Degradation of insulin analogues using duodenum lumen enzymes (prepared by filtration of duodenum lumen content) from SPD rats. The assay is performed by a robot in a 96 well plate (2 mL) with 16 wells available for insulin analogues and standards. Insulin analogues ~15 µM are incubated with duodenum enzymes in 100 mM Hepes, pH=7.4 at 37° C., samples are taken after 1, 15, 30, 60, 120 and 240 min and reaction quenched by addition of TFA. Intact insulin analogues at each point are determined by RP-HPLC. Degradation half time is determined by exponential fitting of the data and normalized to half time determined for the reference insulins, A14E, B25H, desB30 human insulin or human insulin in each assay. The amount of enzymes added for the degradation is such that the half time for degradation of the reference insulin is between 60 minutes and 180 minutes. The result is given as the degradation half time for the insulin analogue in rat duodenum divided by the degradation half time of the reference insulin from the same experiment (relative degradation rate).

TABLE 3

Degradation

| Test compound | Duodenum degradation Relative stability vs. A14E, B25H, desB30 human insulin |
|---|---|
| Compound 1 | 0.7 |

Example 5

Intravenous Rat PK

Anaesthetized rats are dosed intravenously (i.v.) with insulin analogues at various doses and plasma concentrations of the test compound is measured using immunoassays or mass spectrometry at specified intervals for 4 hours or more post-dose. Pharmacokinetic parameters are subsequently calculated using WinNonLin Professional (Pharsight Inc., Mountain View, Calif., USA).

Non-fasted male Wistar rats (Taconic) weighing approximately 200 gram are used. Body weight is measured and rats are subsequently anaesthetized with Hypnorm/Dormicum (each compound is separately diluted 1:1 in sterile water and then mixed; prepared freshly on the experimental day). Anaesthesia is initiated by 2 mL/kg Hypnorm/Doricum mixture sc followed by two maintenance doses of 1 mL/kg sc at 30 minutes intervals, and two maintenance doses of 1 mL/kg sc with 45 minutes intervals. If required in order to keep the rats lightly anaesthetised throughout a further dose(s) 1-2 mL/kg sc is supplied. Weighing and initial anaesthesia is performed in the rat holding room in order to avoid stressing the animals by moving them from one room to another.

TABLE 4

Rat PK

| Test compound | Rat PK i.v. MRT (h) |
|---|---|
| Compound 1 | 24.5 |

Example 6

Dog Intravenous Pharmacokinetic (PK) Profiles

The objective of this protocol is to obtain pharmacokinetic (PK) data from plasma concentration-time profiles of different insulin analogues after intravenous administration to beagle dogs, and to calculate relevant pharmacokinetic parameters for the analogues.

The animals had free access to domestic quality drinking water. The animals were weighed on each day of dosing. Each test substance was given to 3 animals. Consideration had been given to the welfare of individual animals in terms of the number and extent of procedures to be carried out on each animal. A full plasma concentration-time profile was obtained from each animal. During blood sampling, the dogs were placed on a table and fixated by an animal technician sitting beside. This procedure was trained during the acclimatization period. Blood samples, 0.5 mL, were collected into EDTA tubes according to the following schedule:

Predose (−10, 0), and 5, 15, 30, 45, 60, 75, 90, 120, 150, 180, 210, 240, 300, 480, 600, 720, 960, 1440, 1920, 2880, 4320, 5760, 7200, 8640, 10080 minutes.

During periods of frequent sampling, the blood samples were taken from Venflon catheters in cephalic veins kept open with Heparin.saline. The other blood samples were taken from a jugular vein.

Blood samples were kept on ice for max 20 minutes before centrifugation at 4° C. for 4 minutes at 1,300 g.

Plasma was immediately transferred to two micronic tubes, 80 μl plasma in each from each blood sample and placed according to the rack outline. The plasma was stored at −20° C. until assayed.

Plasma concentration-time profiles were analyzed by a non-compartmental pharmacokinetics analysis using Win-Nonlin Professional (Pharsight Inc., Mountain View, Calif., USA).

Calculations were performed using individual concentration-time values from each animal.

TABLE 5

Dog PK

| Test compound | Dog intravenous $T_{1/2} \pm SD$ (hours) | Dog intravenous MRT ± SD (hours) (Mean retention time) |
|---|---|---|
| Compound 1 | 92 ± 22 | 121 ± 28 |

Example 7

Initial Solubility of Compound 1 and Comparison Compound a in the Presence of Zinc Compound 1 and comparison Compound A (i.e. N{Epsilon-B29}-[2-[2-[2-[[2-[2-[2-[[(4S)-4-carboxy-4-(19-carboxynonadecanoylamino)butanoyl]amino]ethoxy]ethoxy]acetyl]-amino]ethoxy]ethoxy]acetyl-][GluA14,HisB16,HisB25],des-ThrB30-Insulin(human); Alternative name: A14E, B16H, B25H, B29K(N$^\epsilon$eicosanedioyl-gGlu-2xOEG), desB30 human insulin, respectively, were dissolved in milli-Q water at a pH value of about 8. Phenol, cresol, zinc acetate (Zn), sodium chloride and glycerol were added in the mentioned order resulting in a final pharmaceutical composition containing: 4.2-5 mM insulin, 1.6% glycerol, 25 mM phenol, 25 mM cresol, pH 7.4 and the zinc and sodium chloride concentration stated in the table below. Pharmaceutical compositions were stored for 24 hours at 22° C. and centrifuged at 15,000×g for 15 minutes. 100 μl of the supernatant was transferred to HPLC vials and concentration determined using acidic gelfiltration as described in Eur. Pharm. NovoRapid. The amount of soluble insulin was determined in percentage of the starting concentration. The accuracy of the measurement was +/−2%.

TABLE 6

Solubility of Compound 1 and comparison Compound A, respectively, in presence of Zn

| Zn/hexamer | 0 mM NaCl Compound A % soluble insulin | 20 mM NaCl Compound A % soluble insulin | 0 mM NaCl Compound 1 % soluble insulin | 20 mM NaCl Compound 1 % soluble insulin |
|---|---|---|---|---|
| 4.5 | 100 | 100 | | 100 |
| 5.5 | 101 | 100 | | 100 |
| 5.9 | | | 100 | |
| 6.5 | 100 | 100 | | 100 |
| 6.6 | | | 100 | |
| 7.4 | | | 100 | |
| 7.5 | 100 | 100 | | 100 |
| 8.3 | | | 100 | |
| 8.5 | 100 | 100 | | 100 |
| 9.2 | | | 100 | |
| 9.5 | 96 | 100 | | 103 |
| 10.0 | | | 100 | |
| 10.5 | 100 | 99 | | 100 |
| 10.9 | | | 100 | |
| 11.5 | 100 | 91 | | 100 |
| 11.8 | | | 100 | |
| 12.5 | 99 | 85 | | 100 |
| 12.7 | | | 100 | |
| 13.5 | 82 | 67 | | 100 |
| 13.6 | | | 100 | |
| 14.4 | | | 100 | |
| 14.5 | 64 | 23 | | 100 |
| 15.3 | | | 100 | |
| 15.5 | 47 | 5 | | 91 |
| 16.2 | | | 92 | |
| 16.5 | 19 | 1 | | 79 |
| 17.1 | | | 13 | |
| 17.5 | 19 | 1 | | 60 |
| 18.5 | 19 | 1 | | 9 |

Conclusion

The comparison compound, in a composition without NaCl, is soluble under the tested conditions in presence of up to 12.5 zinc molecules per hexamer. Comparison Compound A, in a composition with 20 mM NaCl, is soluble under the tested conditions in the presence of up to 10.5 molecules of zinc/hexamer.

Compound 1 is soluble in a composition without NaCl under the tested conditions up to about 15.3 zinc hexamer insulin. Furthermore, Compound 1 is soluble with 20 mM NaCl under the tested conditions up to about 14.5 molecules of zinc per hexamer insulin.

Example 8

Initial Solubility of Human Insulin in the Presence of Zinc

Human insulin was dissolved in milli-Q water at a pH value of about 8. Phenol, cresol, zinc acetate (Zn), sodium chloride and glycerol were added in the mentioned order resulting in a final formulation containing: 4.2-5 mM insulin 1.6% glycerol, 25 mM phenol, 25 mM cresol, pH, 7.4 and the zinc and sodium chloride concentration stated in the table below. The formulations were stored 24 hours at 22° C. and then centrifuged at 15 000×g for 15 min. 100 μl of the supernatant was transferred to HPLC vials and concentration determined on using acidic gelfiltration described in Eur. Pharm. NovoRapid. Amount of soluble insulin was determined in percent of starting concentration.

Accuracy of measurement is +/−2%.

TABLE 7

Solubility of human insulin in the presence of zinc

| Zn/hexamer | 0 mM NaCl % soluble insulin | 20 mM NaCl % soluble insulin |
|---|---|---|
| 2 | 100 | 100 |
| 4 | 100 | 100 |

TABLE 7-continued

Solubility of human insulin in the presence of zinc

| Zn/hexamer | 0 mM NaCl % soluble insulin | 20 mM NaCl % soluble insulin |
|---|---|---|
| 6 | 83 | 100 |
| 8 | 15 | 19 |

Conclusion

Human insulin is soluble in formulations containing up to 6 Zn/insulin hexamer when the formulation contains NaCl and up to 4 Zn/insulin hexamer when the formulation contains close to no NaCl.

Example 9

Chemical and Physical Stability as a Function of Zinc and Sodium Chloride Content The aim of this experiment was to measure the chemical and physical stability of a formulation within the zinc/hexamer window determined by SEC experiments. Furthermore to test if the presence of sodium chloride affected the chemical and/or physical stability.

Formulations

Formulations contained: 3.6 mM of Compound 1, 25 mM phenol, 25 mM cresol, pH 7.4. Zinc and sodium chloride as specified below.

TABLE 8

Zinc containing formulations of Compound 1

| Zinc per hexamer | Sodium chloride mM | Glycerol % w/w |
|---|---|---|
| 5.8 | 20 | 1.6 |
| 5.8 | 75 | 0.7 |
| 5.8 | 120 | 0 |
| 8.1 | 20 | 1.6 |
| 8.1 | 75 | 0.7 |
| 8.1 | 120 | 0 |
| 10.5 | 20 | 1.6 |
| 10.5 | 75 | 0.7 |
| 10.5 | 120 | 0 |

The formulation was prepared as follows:

Compound 1 powder was dissolved in milli-Q water in a stock solution in about the double amount as the final concentration in the formulation. Phenol, cresol, zinc acetate, sodium chloride and glycerol was added in the mentioned order. The resulting solution had a pH about 7.8 and was adjusted to pH 7.4 using 0.2 N HCl, resulting in a final increase in chloride concentration of 1.45 mM Chloride.

The formulation was sterile filtered and filled in 3 ml Cartridges with stoppers.

Physical stability was measured as follows:

Fibrillation tendency was measured in Thioflavin T (THT) assay. Potential precipitation leading to visible particle formation was measured as potential increase in turbidity. Particle formation below 2 μm was measured by dynamic light scattering (DLS). Particle formation above 2 μm was measured by Micro Flow Imaging (MFI).

Chemical stability was measured as increase in High Molecular Weight Particles (HMWP) in percent and decrease in purity as measured by reverse phase UPLC.

Fibrillation Tendency in Thioflavin T Assay

Concentration of Compound 1 was determined according to the method described in WO 2013/153000.

TABLE 9

Lagtimes measured in hours in Thioflavin T assay. Lag time to fibrillation increase as a function of zinc content in the formulation. Formulations containing more than 5.8 zn/hexamer do not fibrillate and has thus a lag time higher than 45 hours.

| Zn/hexamer/mM NaCl | Lag time in hours | Insulin concentration in mM before ThT assay | Insulin concentration in % of starting concentration after ThT assay |
|---|---|---|---|
| 5.8 Zn/hexamer/20 mM NaCl | 15 | 4.3 | 91% |
| 5.8 Zn/hexamer/75 mM NaCl | 14 | 4.2 | 90% |
| 5.8 Zn/hexamer/120 mM NaCl | 15 | 4.2 | 88% |
| 8.1 Zn/hexamer/20 mM NaCl | 45 | 4.3 | 100% |
| 8.1 Zn/hexamer/75 mM NaCl | 45 | 4.2 | 100% |
| 8.1 Zn/hexamer/120 mM NaCl | 45 | 4.1 | 100% |
| 10.5 Zn/hexamer/20 mM NaCl | 45 | 4.0 | 100% |
| 10.5 Zn/hexamer/75 mM NaCl | 45 | 4.2 | 100% |
| 10.5 Zn/hexamer/120 mM NaCl | 45 | 4.2 | 100% |

Quiescent Stability of Compound 1 Probed by DLS

The physical stability of Compound 1 formulated with varying concentrations of NaCl and Zn-acetate stored at 4° C., 37° C. and 45° C. was probed by dynamic light scattering (DLS).

Method

Each sample was measured in triplets on a DynaPro plate reader at 25° C. by recording 20 acquisitions of 10 seconds; data are reported as an average of the three measurements. The samples were not subjected to filtering, but instead they were centrifuged at 15 000×g for 20 min to remove only the very largest flocculates and aggregates, which would otherwise block the measurements. Further, paraffin oil was used for sealing the wells of the DLS microtiter plate instead of the more commonly used plastic foil.

TABLE 10

Protein oligomer average size measured as hydrodynamic diameter (HD) in nm for the different formulations incubated for 2-8 weeks at 4° C., 30° C., 37° C. or 45° C.

| Formulation Zn NaCl | 2 weeks 4° C. | | 8 weeks 4° C. | | 2 weeks 37° C. | | 2 weeks 45° C. | | 8 weeks 30° C. | | 8 weeks 37° C. | |
|---|---|---|---|---|---|---|---|---|---|---|---|---|
| | HR Diam/nm | St. D./nm | HR Diam/nm | St. D./nm | HR Diam/nm | St. D./nm | HR Diam/nm | St. D./nm | HR Diam/nm | St. D./nm | HR Diam/nm | St. D./nm |
| 5.8 Zn/hexamer/ 20 mM NaCl | 4.05 | 0.10 | 3.99 | 0.06 | 3.8 | 0.01 | 3.84 | 0.02 | 4.08 | 0.04 | 4.17 | 0.05 |
| 5.8 Zn/hexamer/ 75 mM NaCl | 5.25 | 0.09 | 5.02 | 0.02 | 4.96 | 0.02 | 4.97 | 0.04 | 5.12 | 0.09 | 5.14 | 0.06 |
| 8.1 Zn/hexamer/ 20 mM NaCl | 3.88 | 0.03 | 3.88 | 0.02 | 3.87 | 0.01 | 3.87 | 0.03 | 3.94 | 0.01 | 4.14 | 0.03 |
| 8.1 Zn/hexamer/ 75 mM NaCl | 5.21 | 0.01 | 5.24 | 0.04 | 5.17 | 0.02 | 5.11 | 0.03 | 5.20 | 0.06 | 5.32 | 0.12 |
| 10.5 Zn/hexamer/ 20 mM NaCl | 4.34 | 0.02 | 4.28 | 0.04 | 4.2 | 0.05 | 4.17 | 0.01 | 4.23 | 0.03 | 4.29 | 0.02 |
| 10.5 Zn/hexamer/ 75 mM NaCl | 5.95 | 0.03 | 5.93 | 0.04 | 5.68 | 0.05 | 5.63 | 0.05 | 5.65 | 0.04 | 5.71 | 0.04 |

HR: Hydrodynamic radius (nm)
Diam: Diameter (nm)
St. D: Standard Deviation

The protein oligomer average size determined with DLS ranges from 3.8 nm (for a formulation with 5.8Zn/insulin hexamer, 20 mM NaCl, at 37° C., after 2 weeks) to 5.95 nm (for a formulation with 10.5 Zn/insulin hexamer, 75 mM NaCl at 4° C., after 2 weeks). For the samples stored at 4° C. the hydrodynamic diameter decreases 1% on average whereas it increased 1 and 4% for the samples stored at 37 and 45° C., respectively. Moreover, all of the recorded auto-correlation functions were compatible with unimodal particle distributions, indicating rather narrow size distributions absent of any large aggregates.

Conclusion

Although the different formulation conditions exhibited noticeable different average oligomer sizes, the change over time was extraordinarily small if present at all, and all formulations appeared to be physically stable at 4° C., 37° C. as well as 45° C. within the 8 week period tested. No aggregates were formed during the period.

Particle Measurement Above 2 μm Using MFI

The formulations were analyzed for sub-visible particle formation in the micrometer range using Micro Flow Imaging (MFI™). Particle counts were generally low, and a large fraction of particles had a dark spherical appearance expected for silicone-oil droplets. However, large translucent flake-like particles appeared in formulations containing 10.5 Zn/hexamer and 150 mM or 75 mM after 2 weeks incubation at 45° C. and 8 weeks at 37° C., respectively.

TABLE 11

Particle concentrations in mL for the different formulations incubated for 2-20 weeks at 4° C., 30° C., 37° C. or 45° C. Particles with Circularity*Aspect Ratio*Intensity STD > 75 and ECD < 3 μm were rejected from the analysis as potentially representing silicone oil.

| Zn/Hex | [NaCl] (mM) | Time | | | | | | | | | |
|---|---|---|---|---|---|---|---|---|---|---|---|
| | | 2 weeks | | | 4 weeks | | 8 weeks | | | 20 weeks | |
| | | 4° C. | 37° C. | 45° C. | 4° C. | 37° C. | 4° C. | 30° C. | 37° C. | 4° C. | 25° C. |
| | | 89.9 | 91.8 | 224.1 | 202.5 | 179.7 | 15.3 | 80.3 | 162.4 | 24.9 | 5.7 |
| 5.8 | 20 | 38.2 | 24.9 | 57.4 | 28.7 | 108.9 | 21.0 | 22.9 | 28.7 | 1.9 | 49.7 |
| 5.8 | 75 | 78.6 | 80.3 | 45.9 | 47.8 | 86.0 | 7.7 | 21.0 | 19.1 | 32.5 | 38.2 |
| 5.8 | 120 | 19.1 | 30.6 | 40.1 | 7.6 | 147.2 | | | | | |
| 8.1 | 20 | 105.1 | 87.9 | 137.6 | 26.8 | 273.2 | 93.6 | 82.2 | 34.4 | 53.5 | 370.5 |
| 8.1 | 75 | 17.2 | 65.0 | 57.3 | 118.5 | 210.2 | 59.3 | 105.1 | 51.6 | 72.6 | 57.3 |
| 8.1 | 120 | 74.6 | 44.0 | 23.0 | 21.0 | 191.1 | | | | | |
| 10.5 | 20 | 158.7 | 78.4 | 152.9 | 230.0 | 326.7 | 137.6 | 290.4 | 131.8 | 13.4 | 17.2 |
| 10.5 | 75 | 63.1 | 203.2 | 154.9 | 225.5 | 221.7 | 120.7 | 126.1 | 586.6 | 28.7 | 44.0 |
| 10.5 | 120 | 80.3 | 343.9 | 1807.6 | 267.5 | 279.0 | | | | | |

TABLE 12

Particle volume fractions (nL particles per mL sample volume) for the different formulations incubated for 2-20 weeks at 4° C., 30° C., 37° C. or 45° C. Particles with Circularity*AspectRatio*Intensity STD > 75 and ECD < 3 μm were rejected from the analysis as potentially representing silicone oil.

| | | Time | | | | | | | | | |
|---|---|---|---|---|---|---|---|---|---|---|---|
| | [NaCl] | 2 weeks | | | 4 weeks | | 8 weeks | | | 20 weeks | |
| Zn/Hex | (mM) | 4° C. | 37° C. | 45° C. | 4° C. | 37° C. | 4° C. | 30° C. | 37° C. | 4° C. | 25° C. |
| | | 0.01 | 0.01 | 0.5 | 0.06 | 0.04 | 0 | 0.03 | 0.02 | 0.01 | 0 |
| 5.8 | 20 | 0 | 0 | 0.12 | 0.03 | 0.03 | 0 | 0 | 0.01 | 0 | 0.04 |
| 5.8 | 75 | 0 | 0.01 | 0.02 | 0 | 0.03 | 0.05 | 0 | 0 | 0.05 | 0.19 |
| 5.8 | 120 | 0 | 0 | 0 | 0 | 0.06 | | | | | |
| 8.1 | 20 | 0.01 | 0 | 0.01 | 0 | 0.02 | 0 | 0.01 | 0 | 0.02 | 0.22 |
| 8.1 | 75 | 0 | 0.01 | 0.06 | 0.01 | 0.01 | 0.03 | 0.02 | 0.01 | 0.01 | 0.01 |
| 8.1 | 120 | 0.02 | 0.01 | 0.03 | 0 | 0.03 | | | | | |
| 10.5 | 20 | 0.01 | 0.01 | 0.02 | 0.02 | 0.08 | 0.09 | 0.06 | 0.03 | 0.06 | 0 |
| 10.5 | 75 | 0.02 | 0.11 | 0.04 | 0.01 | 0.03 | 0.01 | 0.02 | 0.36 | 0.01 | 0.01 |
| 10.5 | 120 | 0.02 | 0.26 | 1.32 | 0.12 | 0.08 | | | | | |

Physical Stability Conclusion

The physical stability was measured as lag time in ThT assay as a function of zinc/hexamer increase with increasing zinc content from 5.8 to 8.1 Zn/insulin hexamer.

Average oligomer size change as measured by DLS revealed no change in oligomer size and no aggregate formation in any of the formulations. Particle measurement as determined by MFI showed increase in particle formation in formulations containing 10.5 Zn/hexamer and 75 mM NaCl.

The physical stability was thus optimal in a formulations containing above 5.8 and below 10.5 Zn/insulin hexamer.

Chemical Stability

HMWP formation was measured using gelfiltration column in acetic acid free eluent as described in WO 2013/153000. HMWP for samples stored at 4° C. was subtracted HMPW for samples stored at 30° C. or 37° C.

TABLE 13

HMWP development for the different formulations incubated for 2-8 weeks at 4° C., 30° C. or 37° C.

| | 2 w 37° C.-<br>2 w 4° C. | 8 w 30° C.-<br>8 w 4° C. | 4 w 30° C.-<br>4 W 4° C. | 8 w 37° C.-<br>8 w 4° C. |
|---|---|---|---|---|
| 5.8 Zn/<br>hexamer/<br>20 mM NaCl | 0.35 | 0.32 | 0.52 | 1.01 |
| 5.8 Zn/<br>hexamer/<br>75 mM NaCl | 0.41 | 0.35 | 0.58 | 1.17 |
| 5.8 Zn/<br>hexamer/<br>120 mM NaCl | 0.40 | 0.34 | | |
| 8.1 Zn/<br>hexamer/<br>20 mM NaCl | 0.25 | 0.22 | 0.43 | 0.75 |
| 8.1 Zn/<br>hexamer/<br>75 mM NaCl | 0.26 | 0.23 | 0.43 | 0.73 |
| 8.1 Zn/<br>examer/<br>120 mM NaCl | 0.28 | 0.31 | | |
| 10.5 Zn/<br>hexamer/<br>20 mM NaCl | 0.28 | 0.32 | 0.45 | 0.76 |

TABLE 13-continued

HMWP development for the different formulations incubated for 2-8 weeks at 4° C., 30° C. or 37° C.

| | 2 w 37° C.-<br>2 w 4° C. | 8 w 30° C.-<br>8 w 4° C. | 4 w 30° C.-<br>4 W 4° C. | 8 w 37° C.-<br>8 w 4° C. |
|---|---|---|---|---|
| 10.5 Zn/<br>hexamer/<br>75 mM NaCl | 0.25 | 0.26 | 0.39 | 0.72 |
| 10.5 Zn/<br>hexamer/<br>120 mM NaCl | 0.28 | 0.23 | | |

Conclusion

Formulations containing 5.8 Zn/insulin hexamer has more HMWP development than formulations containing 8.1 Zn/insulin hexamer or above.

Purity Loss

Loss in purity was measured relative to start. The purity measured by reverse phase chromatography for samples stored at 4° C. was subtracted purity measured for samples stored at 30° C. or 37° C. A UPLC purity method slightly modified relative to method described in WO 2013/153000 was used. In the present instance Waters CSH, C18 column was used which in this case improves the separation and numbers of injections allowed on the column before it has to be changed.

TABLE 14

Loss in purity in % for the different formulations incubated for 2-8 weeks at 4° C., 30° C. or 37° C.

| | 2 w 37° C.-<br>2 w 4° C. | 8 w 30° C.-<br>8 w 4° C. | 4 w 30° C.-<br>4 W 4° C. | 8 w 37° C.-<br>8 w 4° C. |
|---|---|---|---|---|
| 5.8 Zn/<br>hexamer/<br>20 mM NaCl | 1.800 | 1.700 | 3.29 | 6.12 |
| 5.8 Zn/<br>hexamer/<br>75 mM NaCl | 1.500 | 1.300 | 2.86 | 5.44 |
| 8.1 Zn/<br>hexamer/<br>20 mM NaCl | 1.200 | 1.000 | 1.92 | 3.78 |
| 8.1 Zn/<br>hexamer/<br>75 mM NaCl | 1.000 | 1.000 | 1.90 | 3.24 |

TABLE 14-continued

Loss in purity in % for the different formulations incubated for 2-8 weeks at 4° C., 30° C. or 37° C.

| | 2 w 37° C.-2 w 4° C. | 8 w 30° C.-8 w 4° C. | 4 w 30° C.-4 W 4° C. | 8 w 37° C.-8 w 4° C. |
|---|---|---|---|---|
| 10.5 Zn/hexamer/20 mM NaCl | 1.000 | 1.100 | 1.91 | 3.45 |
| 10.5 Zn/hexamer/75 mM NaCl | 0.900 | 0.800 | 1.58 | 3.10 |

Conclusion

The formulations containing 5.8 Zn/insulin hexamer have the highest degradation. Formulations containing 8.1 Zn/insulin hexamer or more have lower degradation. The chemical stability is thus optimal in formulations with 8.1.zinc/hexamer or more. The stability is higher in formulations containing 75 mM NaCl than in formulations containing 20 mM NaCl.

Example 10

The aim of this experiment was to investigate the oligomerisation by size exclusion chromatography as a function of NaCl content in the formulation containing comparative Compound A (i.e. N{Epsilon-B29}-[2-[2-[2-[[2-[2-[2-[[(4S)-4-carboxy-4-(19-carboxy-nonadecanoylamino)butanoyl]amino]ethoxy]ethoxy]acetyl]amino]ethoxy]ethoxy]acetyl]-[GluA14,HisB16,HisB25],des-ThrB30-Insulin (human); Alternative name: A14E, B16H, B25H, B29K (N$^\epsilon$eicosanedioyl-gGlu-2xOEG), desB30 human insulin at 4.2 mM insulin and fixed zinc/insulin hexamer. Furthermore, the aim was to measure the physical and chemical stability.

Formulation

Compound A was dissolved in milli-Q water at a pH value of about 8. Phenol, cresol, zinc acetate (Zn) and glycerol were added in the mentioned order resulting in a final formulation containing: 4.5 Zn/6 insulins, 25 mM phenol, 25 mM cresol, pH 7.4 an insulin concentration of 4.2 mM and sodium chloride (NaCl), zinc acetate and glycerol as stated in the table below.

Physical stability was assessed by measurement of
1. Fibrillation tendency. Measured by Thioflavin T assay. Fibrillation tendency was measured in Thioflavin T (THT) assay as lagtime to fibrillation. THT assay was measured as described on freshly prepared samples; and
2. Oligomer radii in nm and aggregate formation below 4 μm by Dynamic light scattering.

Chemical stability of the formulations were measured as increase in High Molecular Weight Protein (HMWP) increase in insulin related impurities after storage for four weeks (4w) at 37° C. relatively to the amount of HMWP after storage at 4° C.

HMWP was measured using HMWP Method 2 as described in WO 2013/153000.

Formation of insulin related impurities like deamidation compounds was measured using reverse phase chromatography (UPLC).

Amount of monomer was measured in native gel filtration using Method 2 as described in WO 2013/153000 in eluent without phenol.

TABLE 15

HMWP formation and lag time to fibrillation in THT assay of Compound A

| Zink/ins hexamer, NaCl and glycerol content | % monomer SEC Without phenol | % monomer SEC With phenol | HMWP formation (%) 4 w 37° C. | THT lag times (hours) | HMWP Formation (%) 4 w 37° C. |
|---|---|---|---|---|---|
| 4 Zn/hexamer 20 mM NaCl, 1.6% glycerol | 61 | 48 | 0.4 | 15.6 | 0.89 |
| 4 Zn/hexamer 50 mM NaCl, 1.1% glycerol | 49 | 33 | 0.39 | 19.2 | 0.8 |
| 4 Zn/hexamer 75 mM NaCl, 0.7% glycerol | 46 | 30 | 0.43 | 22.0 | 0.81 |
| 4 Zn/hexamer 120 mM NaCl | 45 | 29 | 0.49 | 23.0 | 0.87 |
| 5 Zn/hexamer, 20 mM NaCl, 1.6% glycerol | 78 | 48 | 0.52 | 22.0 | 0.85 |
| 5 Zn/hexamer 50 mM NaCl 1.1% glycerol | 68 | 36 | 0.41 | 27.7 | 0.84 |
| 5 Zn/hexamer 75 mM NaCl 0.7% glycerol | 62 | 32 | 0.40 | 30.9 | 0.79 |
| 5 Zn/hexamer, 120 mM NaCl | 64 | 32 | 0.35 | 29.6 | 0.77 |
| 6 Zn/hexamer 20 mM NaCl 1.6% glycerol | 86 | 44 | 0.35 | 34.2 | 0.8 |
| 6 Zn/hexamer 50 mM NaCl 1.1% glycerol | 77 | 37 | 0.28 | 40.4 | 0.73 |
| 6 Zn/hexamer 75 mM NaCl 0.7% glycerol | 77 | 35 | 0.33 | 45.0 | 0.73 |
| 6 Zn/hexamer 120 mM NaCl | 62 | 28 | 0.40 | 45.0 | 0.73 |
| 7 Zn/hexamer 20 mM NaCl 1.6% glycerol | 58 | 34 | 0.45 | 45.0 | 0.95 |

Conclusion

The amount of Compound A monomer decreases as a function of sodium chloride concentration with a large effect of addition of just up to 50 mM NaCl. Chemical degradation measured as HMWP formation and impurity formation is low in all formulations despite the monomeric content. THT lag times increase with zinc content and sodium chloride content.

TABLE 16

Average hydrodynamic radii $R_h$ avg. in nm and normalized intensity $I_{norm}$ avg. in $10^6$ count/sec (4° C.).

| Insulin | Zink/hexamer, NaCl content and glycerol content | $R_h$ avg. (nm) 2 w | $R_h$ avg. (nm) 4 w | $I_{norm}$ avg. ($10^6$ cts) 2 w | $I_{norm}$ avg. ($10^6$ cts) 4 w |
|---|---|---|---|---|---|
| Degludec | | 1.14 | 1.15 | 1.44 | 1.76 |
| NovoRapid | | 2.49 | 2.49 | 1.94 | 2.27 |
| Compound A | 4 Zn/hexamer 20 mM NaCl, 1.6% glycerol | 2.35 | 2.32 | 7.52 | 7.53 |
| | 4 Zn/hexamer 50 mM NaCl, 1.1% glycerol | 2.96 | 3.02 | 14.7 | 16.1 |
| | 4 Zn/hexamer 75 mM NaCl, 0.7% glycerol | 3.41 | 3.49 | 18.0 | 19.5 |
| | 4 Zn/hexamer 120 mM NaCl | 4.11 | 4.16 | 21.7 | 23.4 |
| | 5 Zn/hexamer 50 mM NaCl 1.1% glycerol | 3.07 | 3.11 | 13.3 | 14.8 |
| | 5 Zn/hexamer 75 mM NaCl 0.7% glycerol | 3.39 | 3.49 | 20.0 | 20.1 |
| | 5 Zn/hexamer 120 mM NaCl | 3.79 | 3.94 | 21.9 | 22.2 |
| | 6 Zn/hexamer 50 mM NaCl 1.6% glycerol | 2.90 | 3.03 | 15.6 | 16.7 |
| | 6 Zn/hexamer 75 mM NaCl 1.1% glycerol | 3.23 | 3.41 | 17.9 | 19.8 |
| | 6 Zn/hexamer 120 mM NaCl 0.7% glycerol | 3.88 | 3.85 | 24.3 | 23.1 |
| | 7 Zn/hexamer 20 mM NaCl 1.6% glycerol | 2.52 | 2.14 | 18.0 | 8.24 |
| | 5 Zn/hexamer 20 mM NaCl, 1.6% glycerol | 2.18 | 2.28 | 7.85 | 6.56 |
| | 6 Zn/hexamer 20 mM NaCl, 1.6% glycerol | 2.04 | 1.99 | 5.64 | 4.65 |

Note:
Samples were not measured at t = 0.
$R_h$ avg. (nm): Average hydrodynamic radii in nm
$I_{norm}$ avg. ($10^6$ cts): Normalized intensity in $10^6$ count/sec (37° C.)

TABLE 17

Average hydrodynamic radii $R_h$ avg. in nm and normalized intensity $I_{norm}$ avg. in $10^6$ count/sec (37° C.).

| Insulin | Zn/hexamer, NaCl content and glycerol content | $R_h$ avg. (nm) 2 w | $R_h$ avg. (nm) 4 w | $I_{norm}$ avg. ($10^6$ cts) 2 w | $I_{norm}$ avg. ($10^6$ cts) 4 w |
|---|---|---|---|---|---|
| Degludec | | 1.14 | 1.14 | 1.44 | 1.50 |
| NovoRapid | | 2.49 | 2.46 | 1.94 | 1.94 |
| Compound A | 4 Zn/hexamer 20 mM NaCl, 1.6% glycerol | 2.35 | 2.26 | 7.52 | 10.6 |
| | 4 Zn/hexamer 50 mM NaCl, 1.1% glycerol | 2.96 | 2.99 | 14.7 | 15.6 |
| | 4 Zn/hexamer 75 mM NaCl, 0.7% glycerol | 3.41 | 3.43 | 18.0 | 18.9 |
| | 4 Zn/hexamer 120 mM NaCl | 4.11 | 4.03 | 21.7 | 23.0 |
| | 5 Zn/hexamer 50 mM NaCl 1.1% glycerol | 3.07 | 3.02 | 13.3 | 16.4 |
| | 5 Zn/hexamer 75 mM NaCl 0.7% glycerol | 3.39 | 3.47 | 20.0 | 19.6 |
| | 5 Zn/hexamer 120 mM NaCl | 3.79 | 3.88 | 21.9 | 21.5 |
| | 6 Zn/hexamer 50 mM NaCl 1.6% glycerol | 2.90 | 2.90 | 15.6 | 15.7 |
| | 6 Zn/hexamer 75 mM NaCl 1.1% glycerol | 3.23 | 3.23 | 17.9 | 18.1 |
| | 6 Zn/hexamer 120 mM NaCl 0.7% glycerol | 3.88 | 3.87 | 24.3 | 22.4 |
| | 7 Zn/hexamer 20 mM NaCl 1.6% glycerol | 2.52 | 2.40 | 18.0 | 12.7 |
| | 5 Zn/hexamer 20 mM NaCl, 1.6% glycerol | 2.18 | 2.11 | 7.85 | 10.7 |
| | 6 Zn/hexamer 20 mM NaCl, 1.6% glycerol | 2.04 | 1.96 | 5.64 | 9.73 |

Note:
Samples were not measured at t = 0.
$R_h$ avg. (nm): Average hydrodynamic radii in nm
$I_{norm}$ avg. ($10^6$ cts): Normalized intensity in $10^6$ count/sec (37° C.)

Conclusion

The hydrodynamic radius increases with increasing salt concentration. Zn concentration has a minor impact on size except at 7 Zn per insulin hexamer. No significant effect on oligomer size and physical stability from incubation temperature.

The invention claimed is:

1. A14E, B16E, B25H, B29K(N(eps)-Eicosanedioyl-gGlu-2xOEG), desB30 human insulin.

2. A method of treating diabetes, comprising administering the compound of claim 1 to a patient in need thereof.

3. The method of claim 2, wherein the compound is administered to the same patient every $2^{nd}$ day or less frequently, and, on average, during a period of time of at least 1 month, 6 months or 1 year, said compound is not administered more frequently to the same patient.

4. The method of claim 2, wherein the compound is administered twice a week, or less frequently, and, on average, during a period of time of at least 1 month, 6 months or 1 year, said compound is not administered more frequently to the same patient.

5. The method of claim 2, wherein the compound is administered once weekly or less frequently, and, on average, during a period of time of at least 1 month, 6 months or 1 year, said compound is not administered more frequently to the same patient.

6. An aqueous solution comprising the compound of claim 1.

7. The aqueous solution according to claim 6, comprising at least 5 zinc ions per insulin hexamer.

8. The aqueous solution according to claim 6, wherein the pH is in the range of from 7 to 8.

9. A pharmaceutical composition comprising the compound of claim 1, and one or more excipients.

10. The pharmaceutical composition according to claim 9, comprising at least 4.5 zinc ions per insulin hexamer.

11. A method of treatment or prevention of diabetes, comprising administering to a subject in need thereof a therapeutically effective amount of the compound of claim 1.

12. The aqueous solution according to claim 7, wherein the pH is in the range of from 7 to 8.

13. The pharmaceutical composition of claim 9, wherein the pH is in the range of from 7-8.

14. The pharmaceutical composition of claim 9, wherein the pH is about 7.4.

15. The pharmaceutical composition of claim 9, comprising at least 5 zinc ions per inulin hexamer.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Modified Insulin A-chain

<400> SEQUENCE: 1

Gly Ile Val Glu Gln Cys Cys Thr Ser Ile Cys Ser Leu Glu Gln Leu
1               5                   10                  15

```
Glu Asn Tyr Cys Asn
            20

<210> SEQ ID NO 2
<211> LENGTH: 29
<212> TYPE: PRT
<213> ORGANISM: Artificial Sequence
<220> FEATURE:
<223> OTHER INFORMATION: Modified Insulin B-chain
<220> FEATURE:
<221> NAME/KEY: MOD_RES
<222> LOCATION: (29)..(29)
<223> OTHER INFORMATION: Lysine(N(epsilon)-Eicosanedioyl-gGlu-2xOEG)

<400> SEQUENCE: 2

Phe Val Asn Gln His Leu Cys Gly Ser His Leu Val Glu Ala Leu Glu
1               5                   10                  15

Leu Val Cys Gly Glu Arg Gly Phe His Tyr Thr Pro Xaa
            20                  25
```